United States Patent
Komazaki et al.

(10) Patent No.: US 10,898,067 B2
(45) Date of Patent: Jan. 26, 2021

(54) ENDOSCOPE APPARATUS

(71) Applicant: OLYMPUS CORPORATION, Tokyo (JP)

(72) Inventors: Iwao Komazaki, Saitama (JP); Takeshi Ito, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 723 days.

(21) Appl. No.: 15/597,306

(22) Filed: May 17, 2017

(65) Prior Publication Data

US 2017/0245746 A1 Aug. 31, 2017

Related U.S. Application Data

(63) Continuation of application No. PCT/JP2014/080361, filed on Nov. 17, 2014.

(51) Int. Cl.
*A61B 1/06* (2006.01)
*A61B 1/005* (2006.01)
(Continued)

(52) U.S. Cl.
CPC ............ *A61B 1/0676* (2013.01); *A61B 1/005* (2013.01); *A61B 1/0051* (2013.01); *A61B 1/06* (2013.01);
(Continued)

(58) Field of Classification Search
CPC ....... A61B 1/0676; A61B 1/0051; A61B 1/06; A61B 1/07; A61B 1/0638; A61B 1/005;
(Continued)

(56) References Cited

U.S. PATENT DOCUMENTS

2007/0112247 A1 5/2007 Hirata
2009/0137952 A1* 5/2009 Ramamurthy ........... A61B 5/06
604/95.01
(Continued)

FOREIGN PATENT DOCUMENTS

| JP | 2005-205195 A | 8/2005 |
|----|---------------|--------|
| JP | 2007-135756 A | 6/2007 |
| JP | 2012-170488 A | 9/2012 |

OTHER PUBLICATIONS

Japanese Office Action dated Jun. 5, 2018 in Japanese Patent Application No. 2016-559710.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope apparatus includes a light source, a bendable insertion section to be inserted into an observation target, a light guide path which is provided in the insertion section and which guides light emitted from the light source, an illumination light emitter which is provided at the distal end of the insertion section and which emits at least some of the light guided by the light guide path to the observation target as illumination light, a curvature sensor which detects a bending shape of at least part of the insertion section, and an illumination light controller which controls an optical characteristic of the illumination light on the basis of the bending shape of the insertion section detected by the curvature sensor.

15 Claims, 18 Drawing Sheets

(51) Int. Cl.
*A61B 1/07* (2006.01)
*G02B 23/26* (2006.01)
*G02B 23/24* (2006.01)

(52) U.S. Cl.
CPC .............. *A61B 1/0638* (2013.01); *A61B 1/07* (2013.01); *G02B 23/2469* (2013.01); *G02B 23/26* (2013.01)

(58) Field of Classification Search
CPC .... A61B 1/00158; A61B 5/062; G02B 23/26; G02B 23/2469
See application file for complete search history.

(56) References Cited

U.S. PATENT DOCUMENTS

| | | | | |
|---|---|---|---|---|
| 2010/0204547 A1* | 8/2010 | Tanaka | ................. | A61B 1/0051 600/145 |
| 2011/0275896 A1* | 11/2011 | Tanaka | ............... | A61B 1/00006 600/118 |
| 2014/0088371 A1* | 3/2014 | Vayser | ............... | A61B 1/00135 600/249 |
| 2015/0091447 A1* | 4/2015 | Kubo | ..................... | A61B 1/045 315/153 |

OTHER PUBLICATIONS

International Search Report dated Feb. 24, 2015 issued in PCT/JP2014/080361.

English translation of International Preliminary Report on Patentability dated Jun. 1, 2017 together with the Written Opinion received in related International Application No. PCT/JP2014/080361.

* cited by examiner

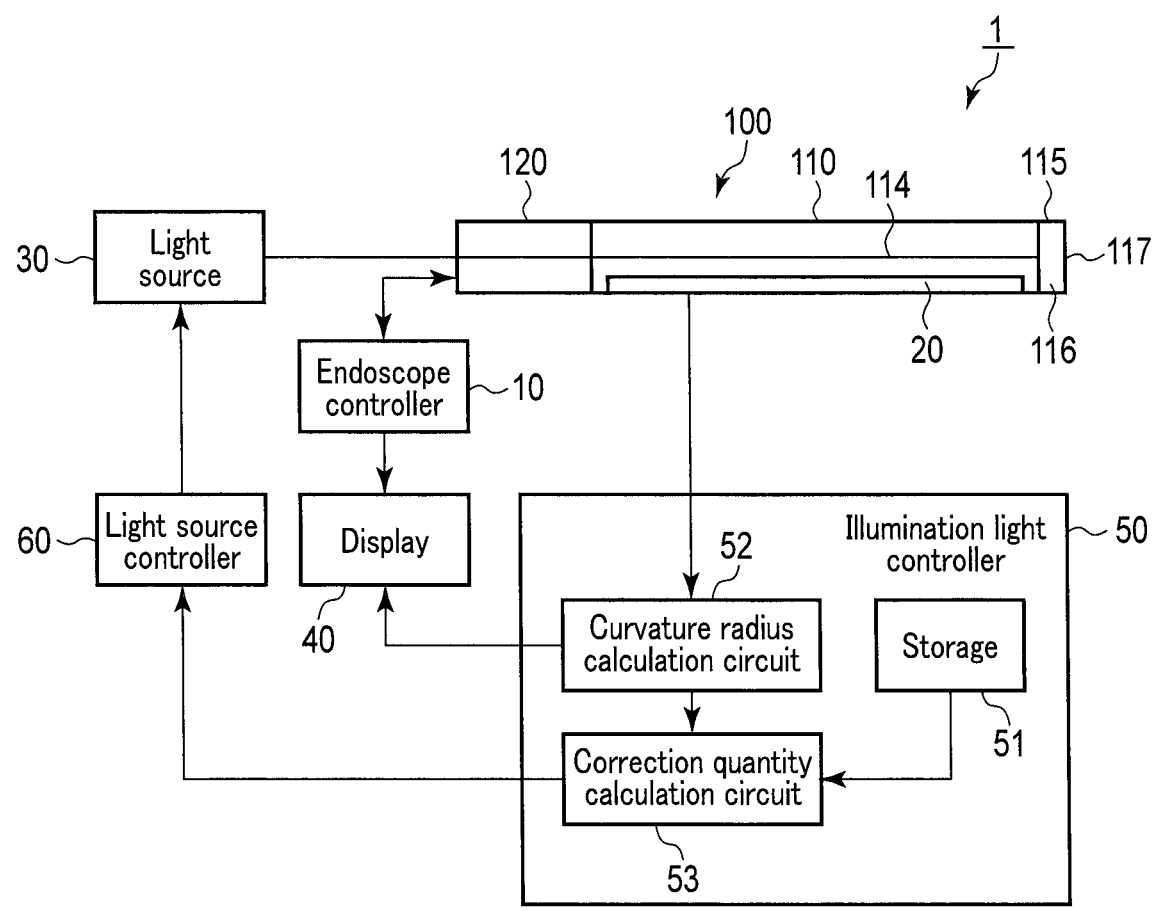
F I G. 1

| R of insertion section 110 (mm) | Illumination light quantity at time of bending (mW) | Change rate (decrease rate) to time of no bending (%) | Drive electric current for light source 30 at no bending (mA) |
|---|---|---|---|
| No bending | 80 | 0 | 200 |
| 20 | 76.3 | 4.6 | |
| 17.5 | 75.2 | 6 | |
| 15 | 73.6 | 8 | |

FIG. 4

| Curvature radius of optical fiber (mm) | Ratio of light quantity to that at time of no bending (%) |
|---|---|
| 20 | 95.5 |
| Interpolation coefficient(/mm) | 0.6 |
| 17.5 | 94 |
| Interpolation coefficient(/mm) | 0.68 |
| 15 | 92.3 |
| Interpolation coefficient(/mm) | 0.8 |
| 12.5 | 90.3 |
| Interpolation coefficient(/mm) | 0.8 |
| 10 | 88.3 |
| Interpolation coefficient(/mm) | 5.32 |
| 7.5 | 75 |

FIG. 5

| Threshold electric current of light source 30 (mA) | Element efficiency of light source 30 $\eta$ (mW/mA) |
|---|---|
| 95 | 0.95 |

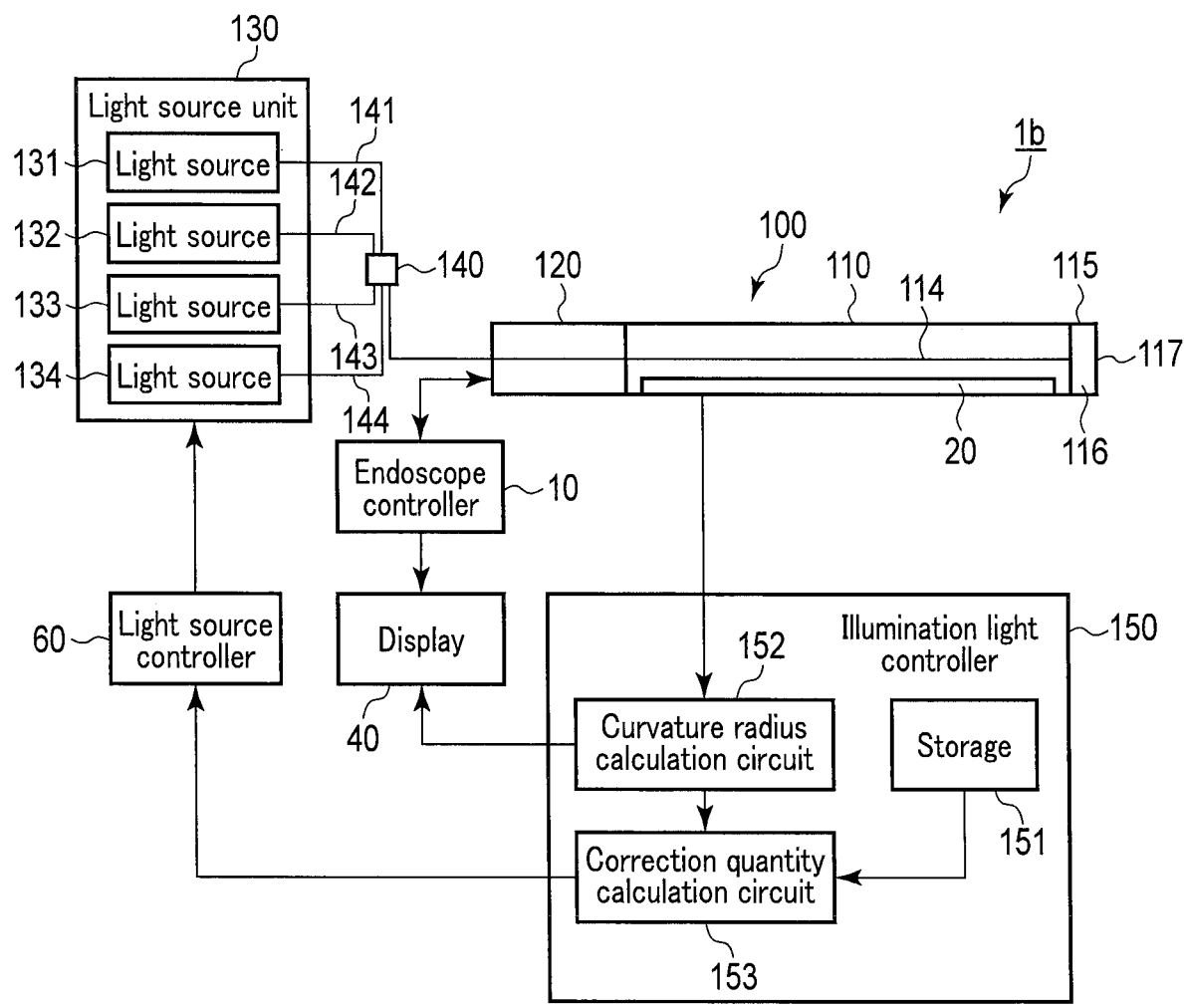
F I G. 13

| R of insertion section 110 (mm) | Quantity of blue light (mW) | Change rate to time of no bending (%) | Drive electric current for light source 131 at time of no bending (mA) |
|---|---|---|---|
| No bending | 200 | 0 | 375 |
| 20 | 191 | 4.5 | |
| 17.5 | 188 | 6 | |
| 15 | 185 | 7.5 | |

F I G. 14

| R of insertion section 110 (mm) | Quantity of green light (mW) | Change rate to time of no bending (%) | Drive electric current for light source 132 at time of no bending (mA) |
|---|---|---|---|
| No bending | 180 | 0 | 500 |
| 20 | 172 | 4.4 | |
| 17.5 | 169 | 6.1 | |
| 15 | 166 | 7.8 | |

F I G. 15

| R of insertion section 110 (mm) | Quantity of red light (mW) | Change rate to time of no bending (%) | Drive electric current for light source 133 at time of no bending (mA) |
|---|---|---|---|
| No bending | 400 | 0 | 500 |
| 20 | 388 | 3 | |
| 17.5 | 385 | 3.75 | |
| 15 | 382 | 4.5 | |

F I G. 16

| R of insertion section 110 (mm) | Quantity of yellow light (mW) | Change rate to time of no bending (%) | Drive electric current for light source 134 at time of no bending (mA) |
|---|---|---|---|
| No bending | 100 | 0 | 500 |
| 20 | 93.4 | 6.6 | |
| 17.5 | 91.1 | 8.9 | |
| 15 | 88.7 | 11.3 | |

F I G. 17

| Curvature radius of optical fiber (mm) | Ratio of light quantity to that at time of no bending (%) |
|---|---|
| 20 | 95.5 |
| Interpolation coefficient(/mm) | 0.6 |
| 17.5 | 94 |
| Interpolation coefficient(/mm) | 0.68 |
| 15 | 92.3 |
| Interpolation coefficient(/mm) | 0.8 |
| 12.5 | 90.3 |
| Interpolation coefficient(/mm) | 0.8 |
| 10 | 88.3 |
| Interpolation coefficient(/mm) | 5.32 |
| 7.5 | 75 |

F I G. 18

| Curvature radius of optical fiber (mm) | Ratio of light quantity to that at time of no bending (%) |
|---|---|
| 20 | 95.5 |
| Interpolation coefficient(/mm) | 0.6 |
| 17.5 | 94 |
| Interpolation coefficient(/mm) | 0.68 |
| 15 | 92.3 |
| Interpolation coefficient(/mm) | 0.8 |
| 12.5 | 90.3 |
| Interpolation coefficient(/mm) | 0.8 |
| 10 | 88.3 |
| Interpolation coefficient(/mm) | 5.32 |
| 7.5 | 75 |

F I G. 19

| Curvature radius of optical fiber (mm) | Ratio of light quantity to that at time of no bending (%) |
|---|---|
| 20 | 97.1 |
| Interpolation coefficient(/mm) | 0.32 |
| 17.5 | 96.3 |
| Interpolation coefficient(/mm) | 0.32 |
| 15 | 95.5 |
| Interpolation coefficient(/mm) | 0.64 |
| 12.5 | 93.9 |
| Interpolation coefficient(/mm) | 0.64 |
| 10 | 92.3 |
| Interpolation coefficient(/mm) | 0.64 |
| 7.5 | 90.7 |

F I G. 20

| Curvature radius of optical fiber (mm) | Ratio of light quantity to that at time of no bending (%) |
|---|---|
| 20 | 93.4 |
| Interpolation coefficient(/mm) | 0.92 |
| 17.5 | 91.1 |
| Interpolation coefficient(/mm) | 0.96 |
| 15 | 88.7 |
| Interpolation coefficient(/mm) | 1.08 |
| 12.5 | 86 |
| Interpolation coefficient(/mm) | 1.12 |
| 10 | 83.2 |
| Interpolation coefficient(/mm) | 1.2 |
| 7.5 | 80.2 |

F I G. 21

| | Threshold electricity supply (mA) | Element efficiency $\eta$ (mW/mA) |
|---|---|---|
| Light source 131 | 110 | 0.95 |
| Light source 132 | 100 | 0.6 |
| Light source 133 | 120 | 1.1 |
| Light source 134 | 80 | 0.42 |
F I G. 22
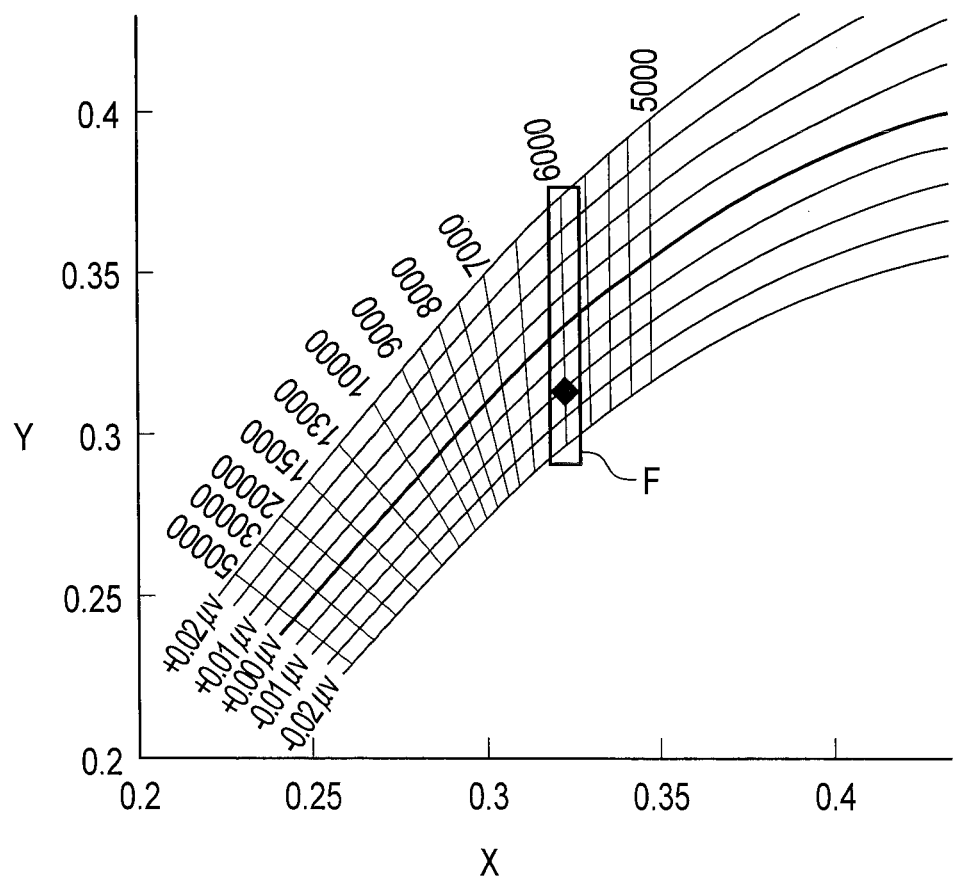
F I G. 23

FIG. 24

| Curvature radius(mm) | Light quantity ratio (converted so that red light is 200) | | | | Color temperature Tc(K) | Color rendering index | Color coordinates(x,y) | |
|---|---|---|---|---|---|---|---|---|
| | Blue light 445nm | Green light 525nm | Red light 640nm | Yellow light 560nm | | | x | y |
| R=20 | | | | | | | | |
| Standard (no bending) | 100 | 90 | 200 | 50 | 6000 | 62.8 | 0.324 | 0.314 |
| No correction | 98 | 86.4 | 200 | 48 | 5800 | 62.8 | 0.326 | 0.311 |
| Light quantity ratio table | 98 | 87 | 200 | 48 | 5810 | 62.8 | 0.326 | 0.312 |
| | 98 | 90 | 200 | 48 | 5900 | 62.8 | 0.325 | 0.315 |
| | 98 | 93 | 200 | 48 | 5980 | 62.8 | 0.323 | 0.318 |
| | 98 | 87 | 200 | 50 | 5810 | 62.8 | 0.326 | 0.314 |
| | 98 | 90 | 200 | 50 | 5815 | 62.8 | 0.325 | 0.317 |
| | 98 | 93 | 200 | 50 | 5970 | 62.8 | 0.324 | 0.32 |
| | 98 | 87 | 200 | 52 | 5810 | 62.8 | 0.327 | 0.316 |
| | 98 | 90 | 200 | 52 | 5810 | 62.8 | 0.325 | 0.319 |
| | 98 | 93 | 200 | 52 | 5970 | 62.8 | 0.324 | 0.321 |
| | 100 | 87 | 200 | 48 | 5950 | 62.8 | 0.325 | 0.309 |
| | 100 | 90 | 200 | 48 | 6000 | 62.8 | 0.323 | 0.312 |
| | 100 | 93 | 200 | 48 | 6050 | 62.8 | 0.323 | 0.312 |
| | 100 | 87 | 200 | 50 | 5920 | 62.8 | 0.322 | 0.315 |
| | 100 | 90 | 200 | 50 | 5930 | 62.8 | 0.325 | 0.311 |
| | 100 | 93 | 200 | 50 | 6050 | 62.8 | 0.324 | 0.314 |
| | 100 | 87 | 200 | 52 | 5820 | 62.8 | 0.325 | 0.313 |
| | 100 | 90 | 200 | 52 | 5970 | 62.8 | 0.324 | 0.316 |
| | 100 | 93 | 200 | 52 | 5980 | 62.8 | 0.323 | 0.319 |

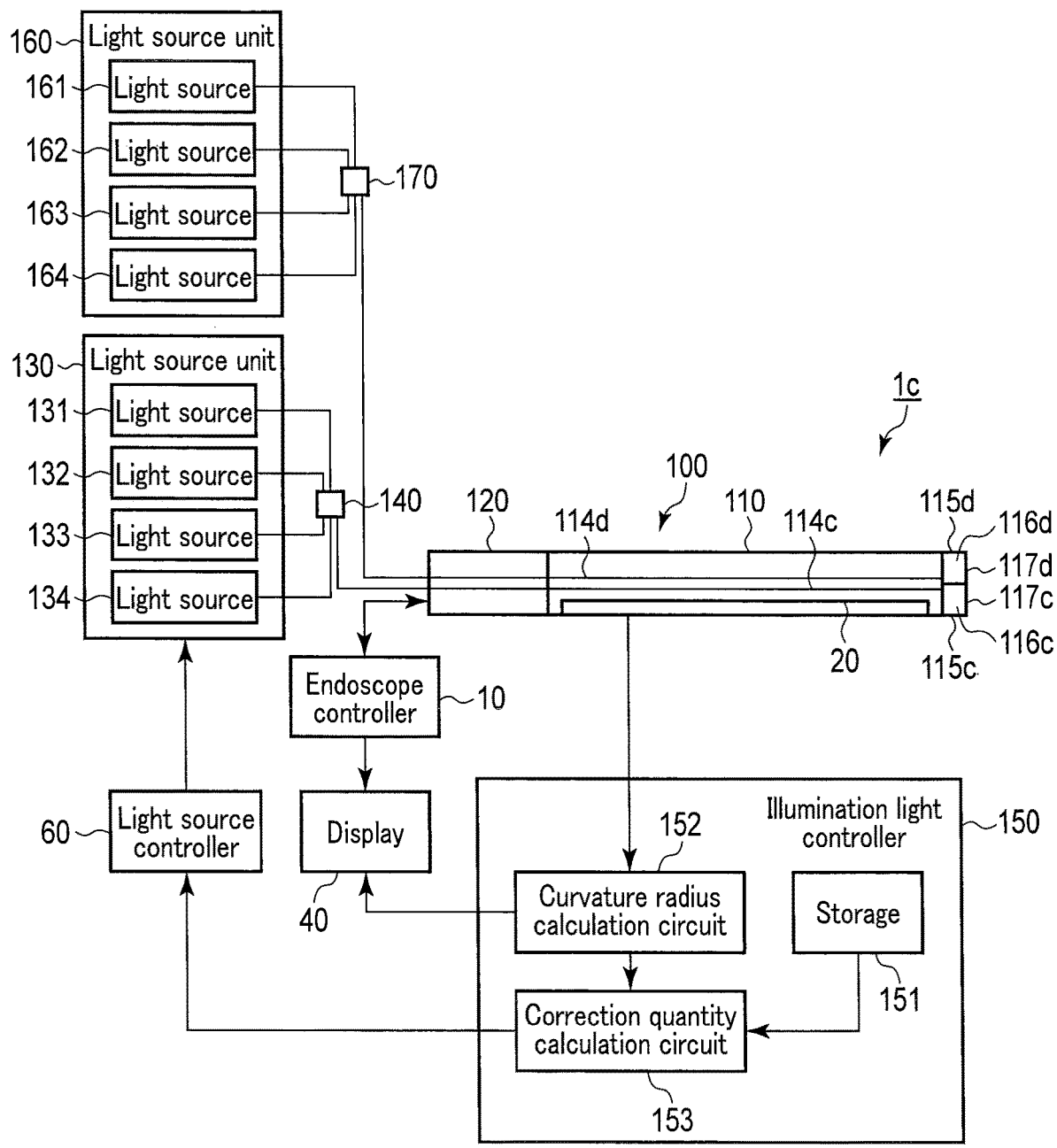
F I G. 25

| Curvature radius of insertion section 110 (mm) | Quantity of blue light (mW) | Quantity of green light (mW) | Quantity of red light (mW) | Quantity of yellow light (mW) | Quantity of illumination light (mW) |
|---|---|---|---|---|---|
| No bending | 160 | 144 | 320 | 80 | 704 |
| 20 | 153 | 137.4 | 310 | 74.5 | 675 |
| 17.5 | 150 | 135 | 307.5 | 72.5 | 666 |
| 15 | 147.4 | 132.7 | 305.3 | 70.8 | 656 |

F I G. 26

| Curvature radius of insertion section 110 (mm) | Quantity of blue light (mW) | Quantity of green light (mW) | Quantity of red light (mW) | Quantity of yellow light (mW) | Quantity of illumination light (mW) |
|---|---|---|---|---|---|
| No bending | 160 | 144 | 320 | 80 | 704 |
| 20 | 151 | 137.4 | 310 | 73 | 671 |
| 17.5 | 148.8 | 134 | 307 | 71.8 | 662 |
| 15 | 146 | 131.5 | 303 | 70 | 650 |

F I G. 27

| Curvature radius of optical fiber (mm) | Ratios of light quantities of light sources 131 and 161 to those at time of no bending (%) | Ratios of light quantities of light sources 132 and 162 to those at time of no bending (%) | Ratios of light quantities of light sources 133 and 163 to those at time of no bending (%) | Ratios of light quantities of light sources 134 and 164 to those at time of no bending (%) |
|---|---|---|---|---|
| 20 | 95.5 | 95.5 | 97.1 | 93.4 |
| Interpolation coefficient(/mm) | 0.6 | 0.6 | 0.32 | 0.92 |
| 17.5 | 94 | 94 | 96.3 | 91.1 |
| Interpolation coefficient(/mm) | 0.68 | 0.68 | 0.32 | 0.96 |
| 15 | 92.3 | 92.3 | 95.5 | 88.7 |
| Interpolation coefficient(/mm) | 0.8 | 0.8 | 0.64 | 1.08 |
| 12.5 | 90.3 | 90.3 | 93.9 | 86 |
| Interpolation coefficient(/mm) | 0.8 | 0.8 | 0.64 | 1.12 |
| 10 | 88.3 | 88.3 | 92.3 | 83.2 |
| Interpolation coefficient(/mm) | 5.32 | 5.32 | 0.64 | 1.2 |
| 7.5 | 75 | 75 | 90.7 | 80.2 |

FIG. 28

| | Threshold electricity supply (mA) | Element efficiency η (mW/mA) |
|---|---|---|
| Light source 131 | 110 | 0.95 |
| Light source 132 | 100 | 0.6 |
| Light source 133 | 120 | 1.1 |
| Light source 134 | 80 | 0.42 |
| Light source 161 | 105 | 0.98 |
| Light source 162 | 96 | 0.7 |
| Light source 163 | 115 | 1.05 |
| Light source 164 | 80 | 0.4 |

ENDOSCOPE APPARATUS

CROSS-REFERENCE TO RELATED APPLICATIONS

This application is a Continuation application of PCT Application No. PCT/JP2014/080361, filed Nov. 17, 2014, the entire contents of all of which are incorporated herein by references.

BACKGROUND OF THE INVENTION

1. Field of the Invention

The present invention relates to an endoscope apparatus which applies illumination light to an observation target to conduct an observation.

2. Description of the Related Art

It is known that in an endoscope apparatus, for example, the wavelength of excitation light emitted from a light source is converted, and illumination light including the wavelength-converted light is then applied to an observation target to conduct an observation. For example, Jpn. Pat. Appln. KOKAI Publication No. 2005-205195 discloses an endoscope apparatus comprising a wavelength converting member which converts the wavelength of excitation light emitted from a light source to send out illumination light of a predetermined wavelength band, and an optical fiber which has a light source at one end and a wavelength converting member at the other end and which guides the excitation light emitted from the light source to the wavelength converting member. The optical fiber is disposed in a flexible insertion section of an endoscope, and the wavelength converting member is disposed at the distal end of the insertion section. In the endoscope apparatus, the light source is a semiconductor laser, and the wavelength converting member is a fluorescent material.

The excitation light emitted from the semiconductor laser propagates through the optical fiber, the fluorescent material converts the wavelength of the excitation light, and the illumination light of the predetermined wavelength band is sent out from the fluorescent material. For example, when use is made of a semiconductor laser having an emission peak wavelength in the vicinity of 400 nm in a short wavelength region of visible light, and a fluorescent material which is a mixture of a fluorescent material emitting blue light and a fluorescent material emitting yellow light, white light which is a mixed light of the blue light and the yellow light sent out from the fluorescent materials will primarily be illumination light. Because light present in the vicinity of 400 nm is difficult to visually recognize, the blue light or the yellow light that are easy to visually recognize, or the white light will be illumination light.

BRIEF SUMMARY OF THE INVENTION

One embodiment of the invention is an endoscope apparatus comprising a light source, a bendable insertion section to be inserted into an observation target, a light guide path which is provided in the insertion section and which guides light emitted from the light source, an illumination light emitter which is provided at the distal end of the insertion section and which emits at least some of the light guided by the light guide path to the observation target as illumination light, a curvature sensor which detects a bending shape of at least part of the insertion section, and an illumination light controller which controls an optical characteristic of the illumination light on the basis of the bending shape of the insertion section detected by the curvature sensor.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a diagram schematically showing an endoscope apparatus according to a first embodiment;

FIG. 4 is an example of a reference table showing the relation between bending state information for an insertion section and the quantity of illumination light;

FIG. 5 is an example of a reference table showing the relation between the curvature radius of an optical fiber and the ratio of the light quantity at a time of no bending;

FIG. 13 is a diagram schematically showing an endoscope apparatus according to a second embodiment;

FIG. 14 is an example of a reference table showing the relation between bending state information for the insertion section and the quantity of illumination light regarding a blue light source;

FIG. 15 is an example of a reference table showing the relation between bending state information for the insertion section and the quantity of illumination light regarding a green light source;

FIG. 16 is an example of a reference table showing the relation between bending state information for the insertion section and the quantity of illumination light regarding a red light source;

FIG. 17 is an example of a reference table showing the relation between bending state information for the insertion section and the quantity of illumination light regarding a yellow light source;

FIG. 18 is an example of a reference table showing the relation between the curvature radius of the optical fiber and the ratio of the light quantity to that at a time of no bending, regarding the blue light source;

FIG. 19 is an example of a reference table showing the relation between the curvature radius of the optical fiber and the ratio of the light quantity to that at a time of no bending, regarding the green light source;

FIG. 20 is an example of a reference table showing the relation between the curvature radius of the optical fiber and the ratio of the light quantity to that at a time of no bending regarding the red light source;

FIG. 21 is an example of a reference table showing the relation between the curvature radius of the optical fiber and the ratio of the light quantity to that at a time of no bending regarding the yellow light source;

FIG. 22 is a table showing an example of information regarding each light source of a light source unit;

FIG. 23 is a graph showing an example of the relation between color temperatures and color coordinates;

FIG. 24 is an example of a table showing the relation between the light quantity ratio, color temperature, and color rendering index of each light source of a light source unit;

FIG. 25 is a diagram schematically showing an endoscope apparatus according to a third embodiment;

FIG. 26 is an example of a reference table showing the relation between bending state information for the insertion section and the quantity of illumination light regarding a first emission window;

FIG. 27 is an example of a reference table showing the relation between bending state information for the insertion section and the quantity of illumination light regarding a second emission window;

FIG. 28 is an example of a reference table showing the relation between the curvature radius of the optical fiber and the ratios of the light quantities to those at times of no bending; and FIG. 29 is a table showing an example of information regarding each light source of the light source unit.

DETAILED DESCRIPTION OF THE INVENTION

First Embodiment (Configuration of Endoscope Apparatus)

Figure 2:
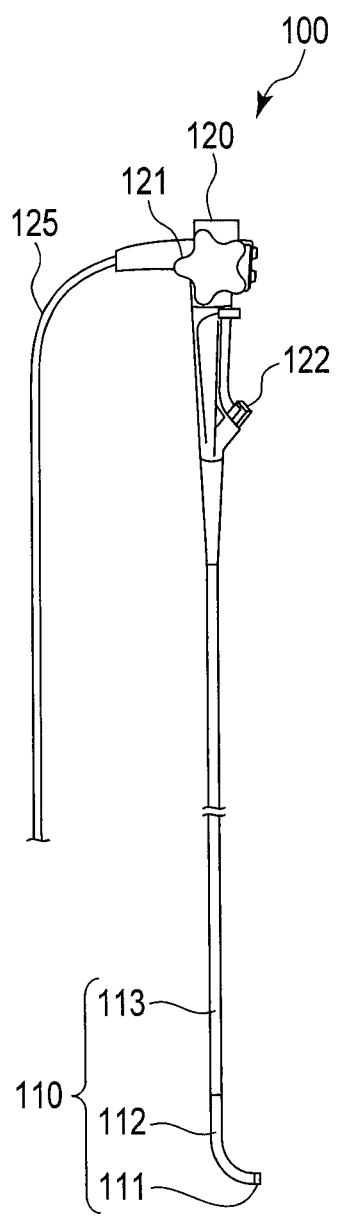
FIG. 2 is a diagram schematically showing the endoscope.

FIG. 1 is a diagram schematically showing an endoscope apparatus 1 according to a first embodiment. The endoscope apparatus 1 has an endoscope 100, an endoscope controller 10, a curvature sensor 20, a light source 30, a display 40, an illumination light controller 50, and a light source controller 60.

(Endoscope)

The endoscope 100 is described with reference to FIG. 1 and FIG. 2. FIG. 2 is a diagram schematically showing the endoscope 100. The endoscope 100 has an elongated insertion section 110 to be inserted into an insertion target, and an operation section 120 provided on the proximal side of the insertion section 110. The insertion section 110 has a distal rigid portion 111, a bending portion 112 provided on the proximal side of the distal rigid portion 111, and a flexible tube portion 113 provided on the proximal side of the bending portion 112. An operation dial 121 is provided in the operation section 120. The distal rigid portion 111 has therein an observation optical system, an image pickup device, and others that are not shown. The bending portion 112 is connected to the operation dial 121 by an unshown operation wire. The operation wire is moved back and forth by the rotation of the operation dial 121, and the bending portion 112 bends in upward, downward, leftward, and rightward directions accordingly. The flexible tube portion 113 has flexibility, and bends in response to external force. Thus, the bending portion 112 can actively bend, and the flexible tube portion 113 can passively bend.

As shown in FIG. 1, a light guide path 114 which guides primary light emitted from the light source 30 is provided inside the insertion section 110. An illumination light emitter 115 is provided in the distal rigid portion 111. The distal end of the light guide path 114 is connected to the illumination light emitter 115. The light guide path 114 is, for example, a single-mode or multimode optical fiber. The optical fiber has flexibility, and bends in accordance with the bending shape of the insertion section 110. In the present embodiment, the optical fiber is a single-wire optical fiber, and a multimode optical fiber having a core diameter of 400 μm or less is used to ensure flexibility at the distal end of the insertion section 110.

The light guide path 114 connected to the illumination light emitter 115 passes through the insertion section 110 and the operation section 120, and is connected to the light source 30 through a universal cord 125 extending from the proximal side of the operation section 120. An image pickup device wiring line connected to the unshown image pickup device in the distal rigid portion 111, and other electric wiring lines also pass through the insertion section 110 and the operation section 120, and are connected to the endoscope controller 10 through the universal cord 125.

An optical characteristic converter 116 which converts the optical characteristics of at least some of the primary light that propagates through the light guide path 114 and then emits secondary light is provided in the illumination light emitter 115. In the present embodiment, the optical characteristic converter 116 is a fluorescent material, and absorbs some of the primary light that is emitted from the light source 30 and propagates through the light guide path 114, and then converts the light into light longer in wavelength than the primary light. That is, the optical characteristic converter 116 converts the wavelength which is one of the optical characteristics of the primary light. In the present embodiment, the primary light is laser light emitted from the light source 30 which is a semiconductor laser, and has coherence, whereas the secondary light emitted from the optical characteristic converter 116 which is a fluorescent material is light having no coherence. That is, the optical characteristic converter 116 converts the coherence of the primary light.

The illumination light emitter 115 has, in its distal end face, an emission window 117. The emission window 117 includes a lens which controls the spread angle of the illumination light, a cover glass to protect the lens, and others. In the illumination light emitter 115, the primary light guided by the light guide path 114 enters the optical characteristic converter 116, is then converted into secondary light, and illumination light including secondary light is applied to the insertion target from the emission window 117.

The operation section 120 also has an insertion port 122. The insertion port 122 is linked to an unshown insertion channel extending through the insertion section 110. For example, at least part of the curvature sensor 20 is inserted through the insertion channel from the insertion port 122.

(Endoscope Controller)

The endoscope controller 10 is connected to the endoscope 100 via the universal cord 125. The endoscope controller 10 includes an image processor, and processes images acquired by the observation optical system and the image pickup device that are mentioned above. The endoscope controller 10 controls various operations of the endoscope 100.

(Curvature Sensor)

The curvature sensor 20 detects the bending shape of at least part of the insertion section 110. The curvature sensor 20 is electrically connected to the illumination light controller 50, and outputs information on the detected bending shape to the illumination light controller 50 as a detection signal. The curvature sensor 20 in the present embodiment is a magnetic sensor 200.

(Magnetic Sensor)

Figure 3:
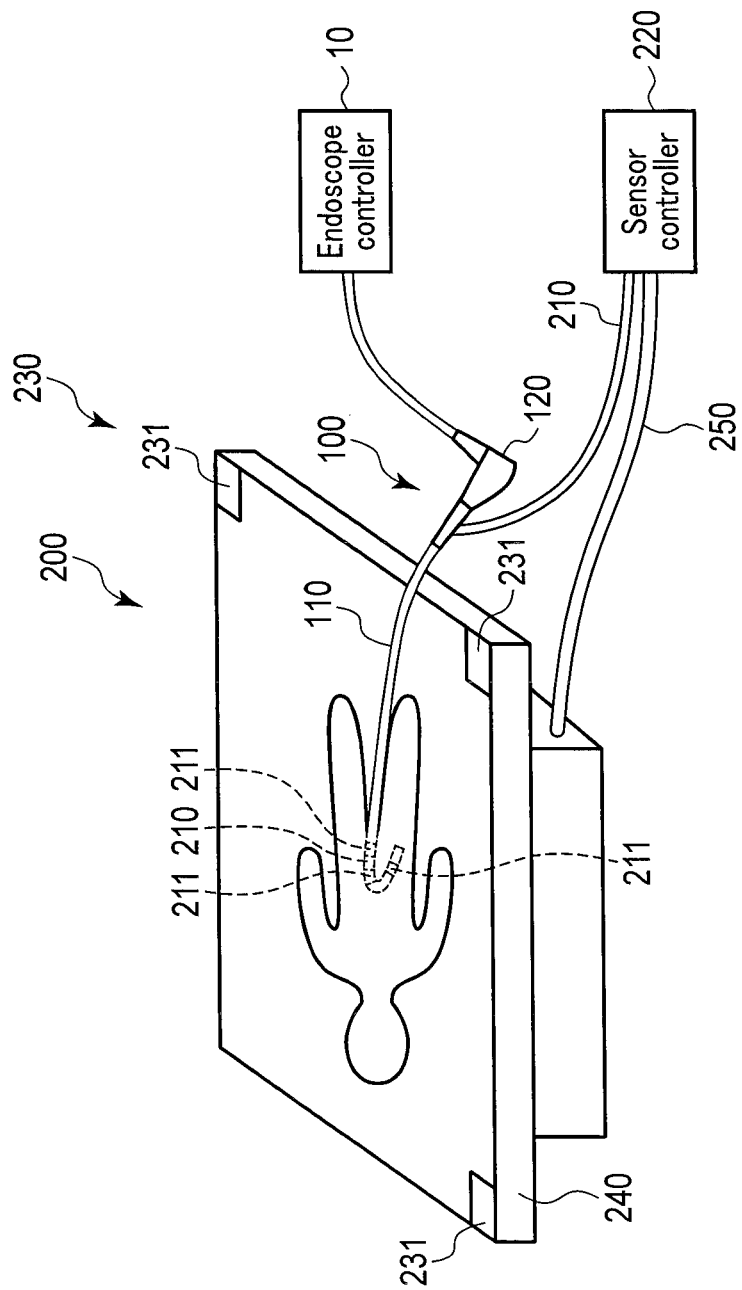
FIG. 3 is a diagram schematically showing a configuration related to a curvature sensor (magnetic sensor) mounted on the endoscope apparatus according to a first embodiment.

The magnetic sensor 200 is described with reference to FIG. 3. FIG. 3 is a diagram schematically showing a configuration related to the magnetic sensor 200 in the endoscope apparatus 1. The magnetic sensor 200 has a probe 210 having at least its part attached to the inside of the insertion section 110. The probe 210 is inserted into the insertion channel from the insertion port 122, and then fixed to the insertion section 110. The probe 210 is connected to a sensor controller 220.

In the probe 210, source coils 211 to generate a magnetic field are spaced out along the longitudinal direction of the insertion section 110 at places of the insertion section 110 where its bending shape needs to be measured. The magnetic sensor 200 has sense coils 230 to detect the magnetic field. The sense coils 230 are, for example, triaxial sense coils 231 provided at predetermined positions, for example, three corners of a bed 240 on which a patient who is the insertion target lies. These triaxial sense coils 231 are connected to the sensor controller 220 via a cable 250 extending from the bed 240.

When the patient lies on the bed 240 and the insertion section 110 is inserted in the body cavity of the patient, the sensor controller 220 generates a magnetic field across the source coils 211. The generated magnetic field is detected by the triaxial sense coils 231, and a detection signal which changes in response to the bending shape of the insertion section 110 is output to the sensor controller 220 from the triaxial sense coils 231. The sensor controller 220 transmits this output signal to the illumination light controller 50.

The magnetic sensor 200 is not limited to the above, and various existing techniques to detect positions by detecting the change of the magnetic field are applicable to the magnetic sensor 200.

(Light Source)

The light source 30 emits primary light toward the proximal end (entrance end) of the light guide path 114. The light source 30 can be a semiconductor light emitting element or lamp, or a component which uses electroluminescent (EL) light as an energy source. The light source 30 is not limited to this, but is preferably a semiconductor laser which is small in size, high in light emitting efficiency, and high in the efficiency of coupling with the light guide path 114. In the present embodiment, a semiconductor laser which emits blue laser light of a wavelength of 445 nm is used as the light source 30.

(Display)

The display 40 is connected to the endoscope controller 10, and displays the image processed in the endoscope controller 10. The display 40 is connected to the illumination light controller 50, and displays the bending shape of the insertion section 110 obtained by the illumination light controller 50, and others.

(Illumination Light Controller)

The illumination light controller 50 is connected to the curvature sensor 20, the display 40, and the light source controller 60. In the present embodiment, the illumination light controller 50 controls light quantity which is one of the optical characteristics of the illumination light.

The illumination light controller 50 has a storage 51. The storage 51 stores light quantity control information indicating the relation between bending shape information for the insertion section 110 corresponding to the output of the curvature sensor 20, and the quantity of the illumination light emitted from the illumination light emitter 115. Strictly speaking, the curvature sensor 20 outputs not the bending shape information for the insertion section 110 but the bending shape information for the curvature sensor 20 (the probe 210 in the case of the magnetic sensor 200). However, the bending shape information for the curvature sensor 20 is regarded as the bending shape information for the insertion section 110 here.

FIG. 4 and FIG. 5 are reference tables showing an example of the light quantity control information stored in the storage 51. As shown in FIG. 4, the storage 51 stores the relation between a curvature radius R of the insertion section 110 corresponding to the output of the curvature sensor 20, the quantity of the illumination light emitted from the illumination light emitter 115 at the curvature radius R, and the change rate (decrease rate), that is, light guiding loss rate of the illumination light quantity at the curvature radius R to that at a time of no bending, and a drive electric current Id of the light source 30 at the time of no bending. The illumination light quantity is an actually measured value acquired by bending the insertion section 110 at the time of shipment or before use. Thus, in the present embodiment, the light quantity control information stored in the storage 51 includes non-bending light quantity control information related to the illumination light quantity in a state where the insertion section 110 is not bent. As shown in FIG. 5, the storage 51 also stores the relation between the curvature radius of the light guide path (optical fiber) 114 and the ratio of the light quantity at the curvature radius R of the insertion section 110 to that at the time of no bending. Although not shown, the storage 51 also stores the relation between the curvature radius of the light guide path (optical fiber) 114 and the change rate (decrease rate) of the emitted light quantity at this curvature radius to that at the time of no bending. This relation is acquired by bending one optical fiber to be the light guide path 114 before or during the manufacture of the endoscope apparatus 1.

The light quantity control information is not exclusively represented in the form of the aforementioned reference tables, and may be represented as a function showing the relation between the bending shape information for the insertion section 110 corresponding to the output of the curvature sensor 20, and the quantity of the illumination light emitted from the illumination light emitter 115, or the like.

Figures 6, 7:
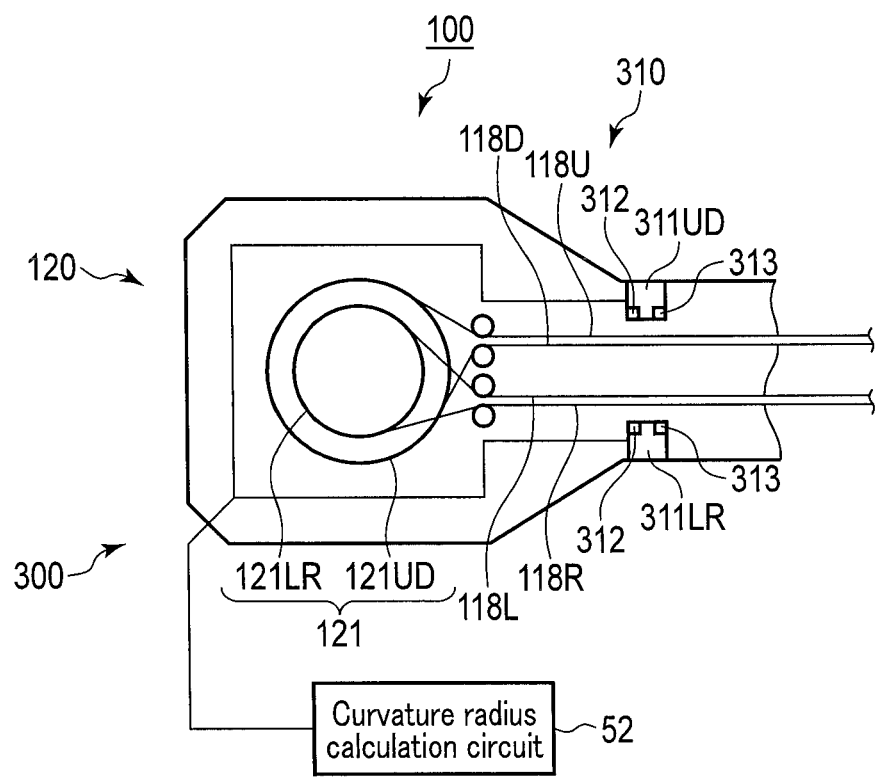
FIG. 6 is a table showing an example of information regarding a light source.
FIG. 7 is a diagram schematically showing a configuration related to the curvature sensor (operation quantity sensor) mounted on the endoscope apparatus according to the first embodiment.

FIG. 6 is a table showing an example of information regarding the light source 30 stored in the storage 51. As shown in FIG. 6, the storage 51 stores a threshold electric current Ith and an element efficiency $\eta$ of the light source 30. The storage 51 also stores the relation between the drive electric current Ith of the light source 30 and light output P, and the relation between a light guiding loss rate $\alpha$ and a drive electric current correction value ΔId (e.g. Equation (1) and Equation (2) described later).

When the wavelength or drive conditions of the light source 30 are changed or when the light source 30 is replaced by a light source different in wavelength or drive conditions, light quantity control information suited to the wavelength and characteristics of the light source to be used needs to be stored in the storage 51. In the present embodiment, the storage 51 is configured so that its memory may be rewritable. The function of the storage 51 may be implemented by a memory (e.g., RAM), a hard disk drive (HDD), or the like.

The illumination light controller 50 has a curvature radius calculation circuit 52. The curvature radius calculation circuit 52 receives the detection signal from the curvature sensor 20, identifies a part of the insertion section 110 which is bent most, and calculates the curvature radius R of the insertion section 110 in this part. The curvature radius R of the part which is bent most is calculated because a light loss quantity of the primary light which propagates through the light guide path 114 is determined by the maximum curvature radius R of the bending shape of the insertion section 110.

The illumination light controller 50 has a correction quantity calculation circuit 53. The correction quantity calculation circuit 53 receives information regarding the curvature radius R of the insertion section 110 calculated by the curvature radius calculation circuit 52. The correction quantity calculation circuit 53 can read the light quantity control information stored in the storage 51. The correction quantity calculation circuit 53 calculates a drive electric current correction value (a correction quantity of the drive electric current of the light source 30) on the basis of the information regarding the curvature radius R of the insertion section 110 and the light quantity control information, and transmits a signal of the drive electric current correction value (drive electric current correction signal) to the light source controller 60.

(Light Source Controller)

The light source controller 60 controls the light emitting state of the light source 30 by controlling the drive electric current or drive voltage of the light source 30. When the quantity of the illumination light emitted from the illumination light emitter 115 changes in accordance with the bending state of the insertion section 110, the light source controller 60 corrects the drive electric current of the light source 30 in response to the drive electric current correction signal output from the correction quantity calculation circuit 53 so that this illumination light quantity will be substantially equal to the illumination light quantity at the time of no bending.

(Operation)

The control operation of the illumination light in the endoscope apparatus 1 according to the first embodiment is described.

When desired primary light is emitted from the light source 30, the emitted primary light is propagated to the optical characteristic converter (fluorescent material) 116 provided in the illumination light emitter 115 through the light guide path 114. The optical characteristic converter 116 absorbs some of the primary light and then converts its wavelength. The rest of the primary light is scattered by the optical characteristic converter 116 without wavelength conversion. As a result, a mixed light of the wavelength-converted light which is secondary light and scattered light which is the primary light scattered without wavelength conversion is emitted from the emission window 117 as illumination light. In the present embodiment, the primary light is blue laser light, the secondary light is yellow wavelength-converted light, and white light which is the mixed light of the above is emitted as the illumination light. The illumination light is controlled by an optical lens provided in the emission window 117 so that the illumination light will have a desired spread angle.

The bending portion 112 bends in the upward, downward, leftward, and rightward directions when an operator operates the operation dial 121. The bending portion 112 bends so that the direction of the distal end of the endoscope, that is, an observation direction is controlled, and an observation target is caught in an observation field of view. The illumination light is then applied to the observation target from the emission window 117 of the illumination light emitter 115, and observation or the like is conducted.

The bending shape of the insertion section 110 changes due to bending (the bending portion 112) resulting from the operation of the operation dial 121 and bending (the flexible tube portion 113) following the shape of the internal space of the observation target. The light guide path 114 attached to the insertion section 110 also changes its bending shape accordingly. In this instance, a light guiding loss caused by the bending is made in the light guide path 114, and the quantity of the illumination light emitted from the illumination light emitter 115 therefore changes. That is, the illumination light quantity is smaller when the insertion section 110 is bent than when the insertion section 110 is in a straight shape. This light loss quantity is determined by the maximum bending angle of the insertion section 110, that is, the light loss quantity is the maximum when the curvature radius R is the minimum.

The curvature sensor 20 outputs the bending shape information for the insertion section 110 to the curvature radius calculation circuit 52 as a detection signal. In response to the detection signal from the curvature sensor 20, the curvature radius calculation circuit 52 calculates the curvature radius R of the part of the insertion section 110 that is bent most, and outputs information on this the curvature radius R to the correction quantity calculation circuit 53. On the basis of this curvature radius R, the correction quantity calculation circuit 53 calculates a drive electric current correction quantity necessary to emit substantially the same quantity of illumination light as the illumination light which is emitted from the illumination light emitter 115 when the insertion section 110 is not bent, by referring to the light quantity control information stored in the storage 51. The correction quantity calculation circuit 53 then outputs the drive electric current correction signal to the light source controller 60. The light source controller 60 controls the drive electric current of the light source 30 on the basis of the drive electric current correction quantity.

Light quantity control by the illumination light controller 50 is described below in more detail with reference to FIG. 4 to FIG. 6.

The correction quantity calculation circuit 53 acquires information regarding the curvature radius R of the insertion section 110 from the curvature radius calculation circuit 52. On the basis of the acquired curvature radius R of the insertion section 110, the correction quantity calculation circuit 53 selects and reads the associated light quantity control information from the storage 51. For example, when the acquired curvature radius R of the insertion section 110 is 20 mm, the correction quantity calculation circuit 53 reads, from the storage 51, an illumination light quantity of 76.3 mW and a change rate of 4.6% corresponding to the curvature radius R of 20 mm, and a drive electric current of 200 mA (FIG. 4) of the light source 30 at a time of no bending. The correction quantity calculation circuit 53 also reads a threshold electric current of the light source 30 of 95 mA and an element efficiency of the light source 30 of 0.95 mW/mA (FIG. 6).

If the drive electric current of the light source 30 at the time of no bending is Ido, the threshold electric current to drive the light source 30 is Ith, and the element efficiency is η, then the relation between the drive electric current Id and the light output P is represented by Equation (1) below.

$$P=\eta \times (Id-Ith) \qquad \text{Equation (1)}$$

If the light guiding loss rate is α (%), the drive electric current correction value ΔId is represented by Equation (2) below.

$$\Delta Id=\alpha/100 \times (Ido-Ith) \qquad \text{Equation (2)}$$

Equation (1) and Equation (2) are also stored in the storage 51, and read by the correction quantity calculation circuit 53.

On the basis of the light quantity control information and Equation (1) and Equation (2) that have been read, the correction quantity calculation circuit 53 calculates the drive electric current correction value ΔId to increase the light output P of 4.6% corresponding to the light guiding loss rate. The correction quantity calculation circuit 53 then transmits the drive electric current correction signal to the light source controller 60.

Alternatively, the correction quantity calculation circuit 53 reads, from the storage 51, an illumination light quantity of 76.3 mW and a change rate of 4.6% corresponding to the curvature radius R of 20 mm, a drive electric current of 200 mA (FIG. 4) of the light source 30 at the time of no bending, a threshold electric current of the light source 30 of 95 mA, and an element efficiency of the light source 30 of 0.95 mW/mA (FIG. 6), and the correction quantity calculation circuit 53 then checks the read change rate against the light quantity control information shown in FIG. 5 to estimate the curvature radius of one light guide path (optical fiber) 114 corresponding to the curvature radius R of the insertion section 110. For example, because the change rate of the illumination light when the curvature radius R of the insertion section 110 is 20 mm is 4.6%, the ratio of the light quantity to that at the time of no bending is 95.4%. From the light quantity control information shown in FIG. 5, the correction quantity calculation circuit 53 estimates the corresponding curvature radius of the optical fiber by using an interpolation coefficient. Here, the interpolation coefficient in the reference table shown in FIG. 5 is (the change quantity of the ratio of the light quantity to that at the time of no bending)/(the change quantity of the curvature radius). When the curvature radius R of the insertion section 110 is 20 mm, the curvature radius of the optical fiber estimated by the correction quantity calculation circuit 53 is 19.8 mm.

Thus, the curvature radius R (20 mm) of the insertion section 110 calculated by the curvature radius calculation circuit 52 does not necessarily correspond to the estimated curvature radius (19.8 mm) of the light guide path 114. Therefore, for stricter illumination light control, the correction quantity calculation circuit 53 estimates the curvature radius of the light guide path 114 on the basis of the curvature radius R of the insertion section 110 calculated by the curvature radius calculation circuit 52 as described above, and further reads the light guiding loss rate corresponding to the curvature radius of the light guide path 114. The correction quantity calculation circuit 53 then uses this light guiding loss rate to calculate the aforementioned drive electric current correction value ΔId, and then transmits the drive electric current correction signal to the light source controller 60.

The light source controller 60 increases the output of the laser light by the light source 30 on the basis of the drive electric current correction value ΔId. The increase of the output compensates for the light loss caused by the bending of the insertion section 110, so that the illumination light quantity is kept at a predetermined value. That is, even when the insertion section 110 is bent, the endoscope apparatus 1 emits illumination light substantially equal to that in the case of no bending, that is, in a non-bending state. In this instance, the change of the light quantity is preferably within a range that does not interfere with the observation. That is, it is preferable to keep the change of the light quantity in or below a light quantity change allowable range. Although the light quantity change allowable range varies according to observation purposes, keeping the change to 5% or less enables a satisfactory observation environment. Keeping the change to 10% or less enables a substantially satisfactory observation environment.

Advantageous Effects

In the present embodiment, even if the insertion section 110 bends, the drive electric current correction signal is transmitted to the light source controller 60 from the correction quantity calculation circuit 53 to compensate for the bending-caused light loss of the primary light emitted from the light source 30. Thus, the quantity of the primary light emitted from the light source 30 is increased, and the quantity of the illumination light emitted from the illumination light emitter 115 is kept at a predetermined value (allowable range) at the time of no bending. Therefore, it is possible to provide the endoscope apparatus 1 which emits desired illumination light from the illumination light emitter 115, that is, which can stably obtain the illumination light quantity, regardless of the bending state of the insertion section 110.

The correction quantity calculation circuit 53 estimates the curvature radius of the light guide path 114 and the corresponding light guiding loss rate from the curvature radius R of the insertion section 110 calculated by the curvature radius calculation circuit 52, and can transmit the drive electric current correction signal to the light source controller 60 accordingly to compensate for the bending-caused light loss. Consequently, it is possible to conduct stricter illumination light control.

For example, when the endoscope 100 in which the insertion section 110 is relatively small in diameter is used (when the curvature radius calculated on the basis of the output of the curvature sensor 20 can be considered substantially equal to the curvature radius of the light guide path 114), the operator of the endoscope apparatus 1 finds the drive electric current correction value on the basis of the curvature radius R of the insertion section 110 calculated by the curvature radius calculation circuit 52. When the endoscope 100 in which the insertion section 110 is relatively large in diameter is used (when the light guiding loss rate is out of the allowable range due to the difference between the curvature radius calculated on the basis of the output of the curvature sensor 20 and the curvature radius of the light guide path 114), the operator of the endoscope apparatus 1 further estimates the curvature radius of the light guide path 114 at the curvature radius R from the curvature radius R of the insertion section 110 calculated by the curvature radius calculation circuit 52, and finds the drive electric current correction value on the basis of the curvature radius of the light guide path 114. According to the present embodiment, the operator makes such a selection, and illumination light control suitable to various endoscopes can therefore be performed.

Although the magnetic sensor 200 is shown as the curvature sensor 20 in the above explanation, the curvature sensor 20 may be a sensor other than the magnetic sensor. In the case described below, an operation quantity sensor 300 or a fiber sensor 400 is used as the curvature sensor 20 instead of the magnetic sensor 200.

(Operation Quantity Sensor)

The operation quantity sensor 300 is described with reference to FIG. 7. FIG. 7 is a diagram schematically showing a configuration related to the operation quantity sensor 300 in the endoscope apparatus 1. The operation quantity sensor 300 has a bending operation quantity detector 310 which detects the operation quantities of the operation dial 121 (121LR and 121UD) of the endoscope 100. The operation quantities of the operation dial 121 are the motion quantities (rotation quantities) of the operation dials 121LR and 121UD to bend the bending portion 112, and correspond to the movement quantities of operation wires 118L, 118R, 118U, and 118D. The operation dial 121LR is connected to the bending portion 112 by the operation wires 118L and 118R, and bends the bending portion 112 in the leftward and rightward directions by its rotational operation. The operation dial 121UD is connected to the bending portion 112 by the operation wires 118U and 118D, and bends the bending portion 112 in the upward and downward directions by its rotational operation.

The bending operation quantity detector 310 has bending operation quantity sensors 311LR and 311UD to detect the bending operation quantities of the operation dials 121LR and 121UD. Each of the bending operation quantity sensors 311LR and 311UD has a light emitter 312 which applies light to movable parts of the operation dials 121LR and 121UD, and a light receiver 313 which receives the light from the movable parts of the operation dials 121LR and 121UD to acquire images of the movable parts. The acquired images of the movable parts are transmitted to, for example, the curvature radius calculation circuit 52 and then processed, and the bending shape (curvature radius R) of the bending portion 112 is calculated on the basis of the motion quantities of the movable parts.

In one example, as shown in FIG. 7, the bending operation quantity sensor 311LR targets one of the operation wires 118L and 118R for reading. The bending operation quantity sensor 311UD targets one of the operation wires 118U and 118D for reading. That is, the bending operation quantity sensor 311LR applies light to one of the operation wires 118L and 118R to acquire its image, and processes this image to directly detect its movement quantity. Similarly, the bending operation quantity sensor 311UD applies light to one of the operation wires 118U and 118D to acquire its image, and processes this image to directly detect its movement quantity.

Moreover, it is also possible to detect the operation quantity of the operation dial 121 by a sensor such as an encoder. Such a configuration permits the bending quantity of the bending portion 112 to be detected without any sensor mounted on the insertion section 110. It is also possible to detect the bending quantity of the insertion section 110 by use of an X-ray camera or the like.

(Fiber Sensor)

Figure 8:
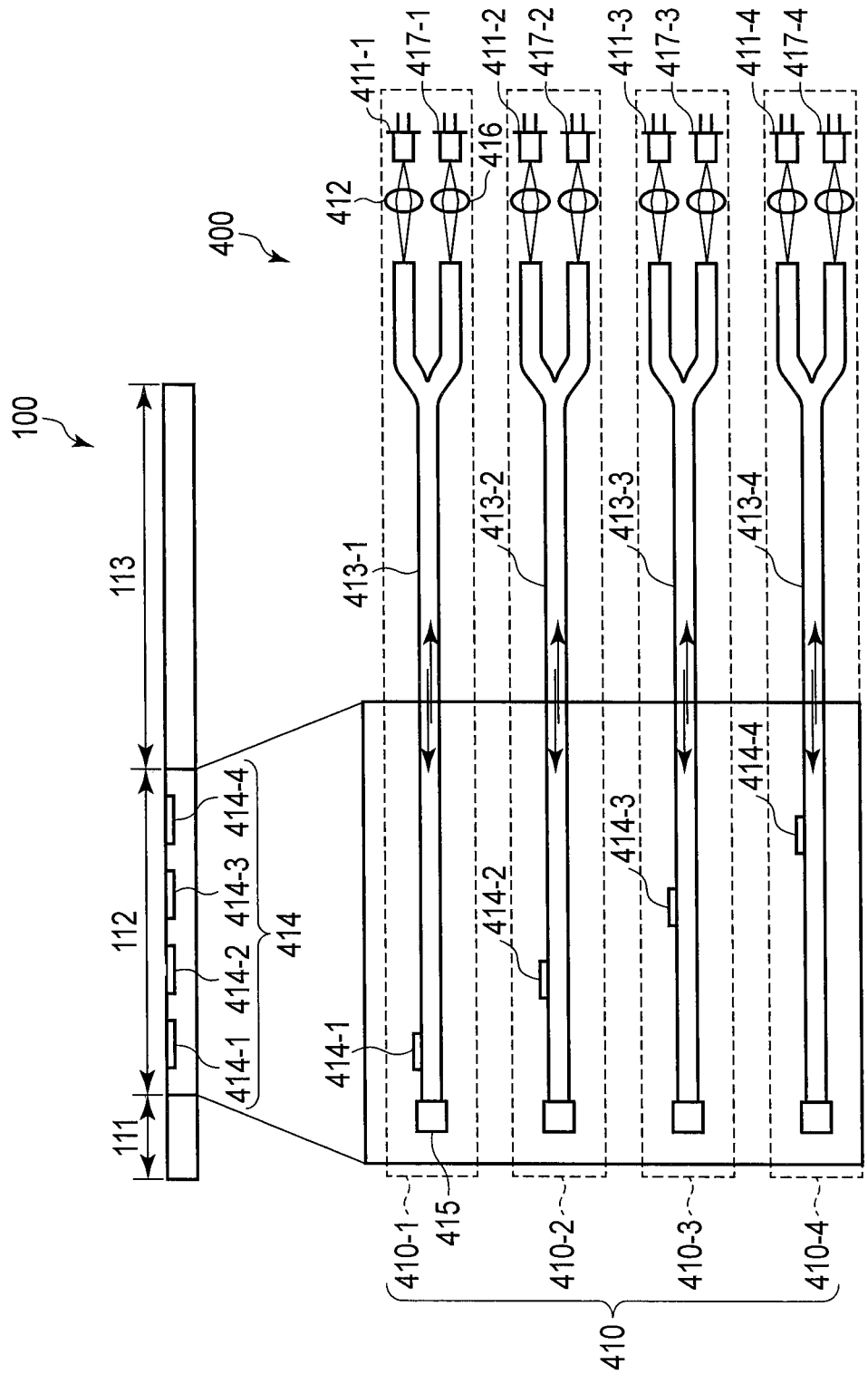
FIG. 8 is a diagram schematically showing a configuration related to a curvature sensor (fiber sensor) mounted on the endoscope apparatus according to the first embodiment.

The fiber sensor 400 is described with reference to FIG. 8. FIG. 8 is a diagram schematically showing a configuration related to the fiber sensor 400 in the endoscope apparatus 1. The fiber sensor 400 is a sensor that uses a bending loss of the optical fiber, and comprises, for example, fiber sensor elements 410-1, 410-2, 410-3, and 410-4. The fiber sensor elements 410-1, 410-2, 410-3, and 410-4 have optical fibers 413-1, 413-2, 413-3, and 413-4 incorporated in the insertion section 110, respectively. These optical fibers bend integrally with the insertion section 110. Detection targets 414-1, 414-2, 414-3, and 414-4 are formed in the optical fibers 413-1, 413-2, 413-3, and 413-4, respectively. The respective detection targets 414-1, 414-2, 414-3, and 414-4 are staggered in the longitudinal direction of the insertion section 110.

In the respective fiber sensor elements 410-1, 410-2, 410-3, and 410-4, the input ends (proximal ends) of the optical fibers 413-1, 413-2, 413-3, and 413-4 are branched. Light emitted from each of light sources 411-1, 411-2, 411-3, and 411-4 enters one end of this branch via a lens 412, propagates through each of the optical fibers 413-1, 413-2, 413-3, and 413-4, and is reflected by a mirror 415 disposed at the distal end, and the reflected light is again detected by each of photodetectors 417-1, 417-2, 417-3, and 417-4 via an optical fiber 406, the other end of the branch, and a lens 416. Light quantity information detected in the photodetectors 417-1, 417-2, 417-3, and 417-4 is output to the curvature radius calculation circuit 52.

When the light which propagates through the optical fibers 413-1, 413-2, 413-3, and 413-4 passes in the vicinity of the detection targets 414-1, 414-2, 414-3, and 414-4, the quantity of this light changes at their positions in accordance with the bending state of the bending portion 112. Therefore, the bending shape of not only the fiber sensor 400 but also the bending portion 112 is detected by the light quantity detected in the photodetectors 417-1, 417-2, 417-3, and 417-4.

The fiber sensor 400 (the optical fibers 413-1, 413-2, 413-3, and 413-4) is smaller in diameter than the magnetic sensor 200 (the probe 210), and can therefore be also incorporated in an endoscope in which the insertion section 110 is small in diameter. The use of the fiber sensor 400 enables the curvature sensor 20 which requires no antenna (sense coil).

First Embodiment: Modification

A modification of the first embodiment is described with reference to FIG. 9 to FIG. 12. In the present modification, the illumination light controller 50 controls light quantity and light quantity distribution (light distribution) as the optical characteristics of the illumination light. The differences between the first embodiment and the modification are only described, and the same configurations are not described.

Figure 9:
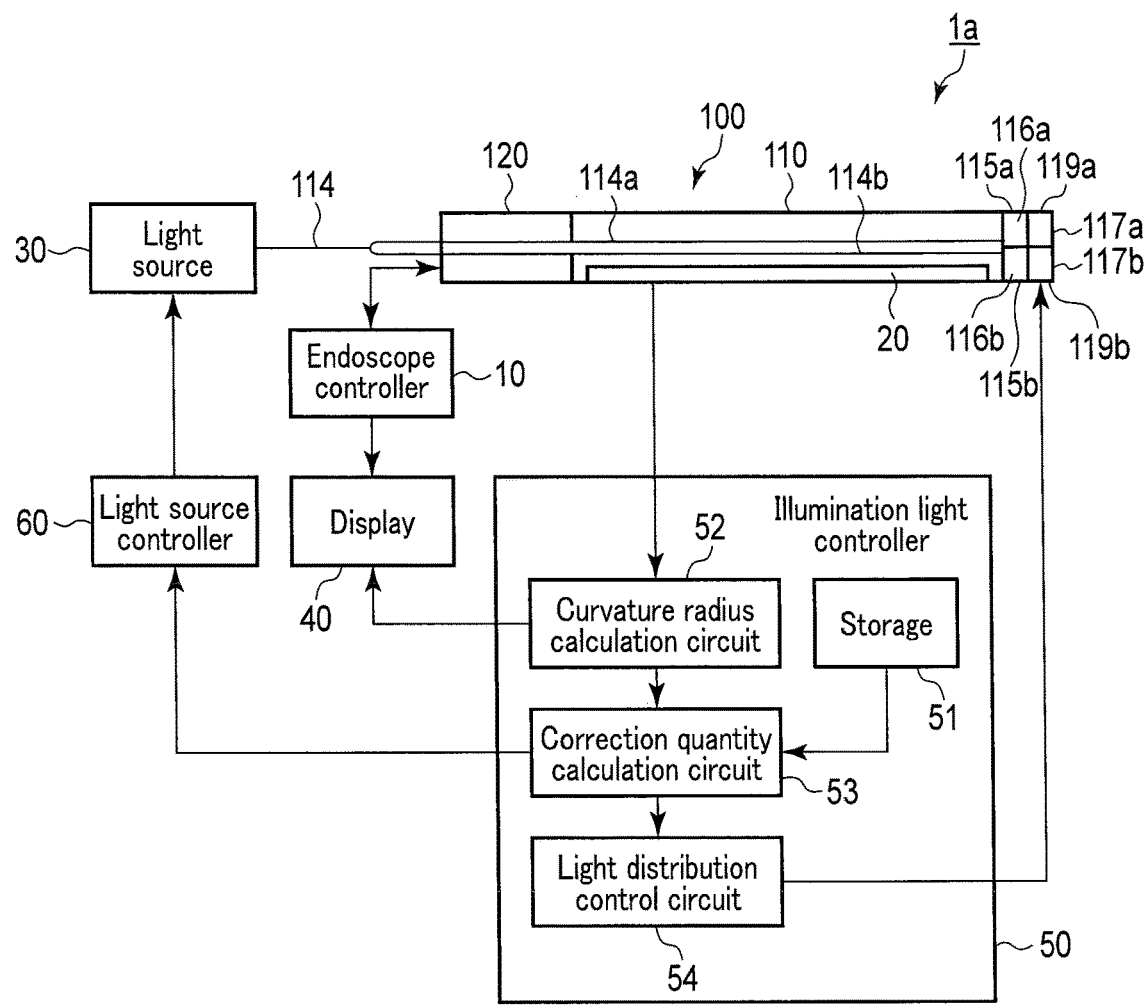
FIG. 9 is a diagram schematically showing an endoscope apparatus according to a modification of the first embodiment.

FIG. 9 is a diagram schematically showing an endoscope apparatus 1a according to the present modification. The difference between the first embodiment and the present modification is that the light guide path 114 through which the light emitted from the light source 30 propagates braches into a first light guide path 114a and a second light guide path 114b along the way. The light guide path 114 is configured by direct fusion connection of core parts of one single-wire optical fiber and two single-wire optical fibers (1×2 branch fiber), or by fusion connection of parts of the cores of two single-wire optical fibers (2×2 optical coupler). The light quantity ratio between the first light guide path 114a and the second light guide path 114b after branching is set substantially at 1:1. This ratio is desirable for smaller wavelength dependence of light that propagates. In the 2×2 optical coupler, the light emitted from the light source 30 may be guided into one of the optical fibers on the input side, and a photodetector may be provided in the other optical fiber on the input side and used as a monitor of the quantity of the light emitted from the light source 30.

Illumination light emitters 115a and 115b are provided at the distal ends of the light guide paths 114a and 114b, respectively. Optical characteristic converters (fluorescent materials) 116a and 116b independent of each other are provided in the illumination light emitters 115a and 115b, respectively. In the present modification, light distribution control members 119a and 119b to adjust the light quantity distributions (light distribution characteristic) of the illumination light emitted from emission windows 117a and 117b are further provided in the illumination light emitters 115a and 115b, respectively. The light distribution control members 119a and 119b are, for example, electronic diaphragms or variable-focus lenses. The electronic diaphragms change their opening diameters to adjust the light quantity and light quantity distribution of the illumination light. In the variable-focus lenses, if the voltage applied to a liquid lens portion is changed, the outer form (shape) of the liquid lens changes accordingly. The voltage applied to the liquid lens is previously set to a predetermined application voltage, and the shape of the liquid lens is set to a collecting lens shape, so that the focal distance changes and the light quantity distribution of the illumination light is adjusted if a correction voltage is applied to change the application voltage.

Figure 10:
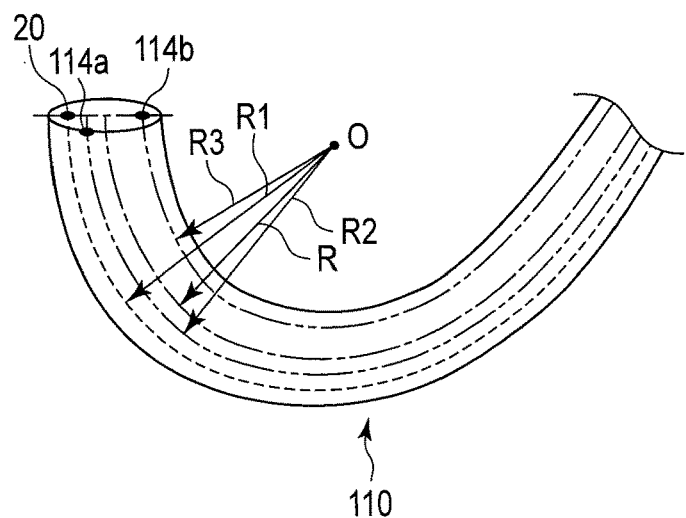
FIG. 10 is a diagram showing the positional relation between the curvature sensor, a first light guide path, and a second light guide path in the insertion section.

The storage 51 stores information on the positional relation between the first light guide path 114a, the second light guide path 114b, and the curvature sensor 20 in the insertion section 110. FIG. 10 is a diagram showing an example of the positional relation between these parts in the insertion section 110. In the bending state shown in FIG. 10, R1>R2>R3, wherein R is the curvature radius of the insertion section 110, R1 is the curvature radius of the curvature sensor 20, R2 is the curvature radius of the first light guide path 114a, and R3 is the curvature radius of the second light guide path 114b.

In the present modification, the storage 51 stores bending state information for the insertion section 110 corresponding to the output of the curvature sensor 20 for each emission window, and light quantity control information indicating the relation between the light quantities of the illumination lights emitted from the illumination light emitters 115a and 115b for each emission window.

The illumination light controller 50 has a light distribution control circuit 54. The light distribution control circuit 54 is electrically connected to the light distribution control members 119a and 119b which are respectively provided in the illumination light emitters 115a and 115b and which can electrically vary the light distribution characteristic.

(Operation)

In response to a detection signal from the curvature sensor 20, the curvature radius calculation circuit 52 calculates the curvature radius R1 of the curvature sensor 20. The curvature radius calculation circuit 52 further reads the information on the positional relation between the first light guide path 114a, the second light guide path 114b, and the curvature sensor 20 stored in the storage 51. The curvature radius calculation circuit 52 then calculates the curvature radius R2 of the first light guide path 114a and the curvature radius R3 of the second light guide path 114b on the basis of the curvature radius R1 of the curvature sensor 20 and the read positional relation information, and outputs information on the curvature radii R2 and R3 to the correction quantity calculation circuit 53.

The correction quantity calculation circuit 53 calculates a drive electric current correction quantity on the basis of the curvature radii R2 and R3. For example, R2<R3 in the case of the bending state shown in FIG. 10, so that the correction quantity calculation circuit 53 calculates the drive electric current correction quantity to compensate for the light loss quantity of the first light guide path 114a having a smaller curvature radius. A drive electric current correction signal is then transmitted to the light source controller 60 from the correction quantity calculation circuit 53 so that the light source controller 60 increases the drive electric current of the light source 30. As a result, the quantity of the illumination light corresponding to the first light guide path 114a having a smaller curvature radius returns to the quantity in a non-bending state. However, the quantity of the illumination light corresponding to the second light guide path 114b having a greater curvature radius increases compared to that in a non-bending state.

Figure 11:
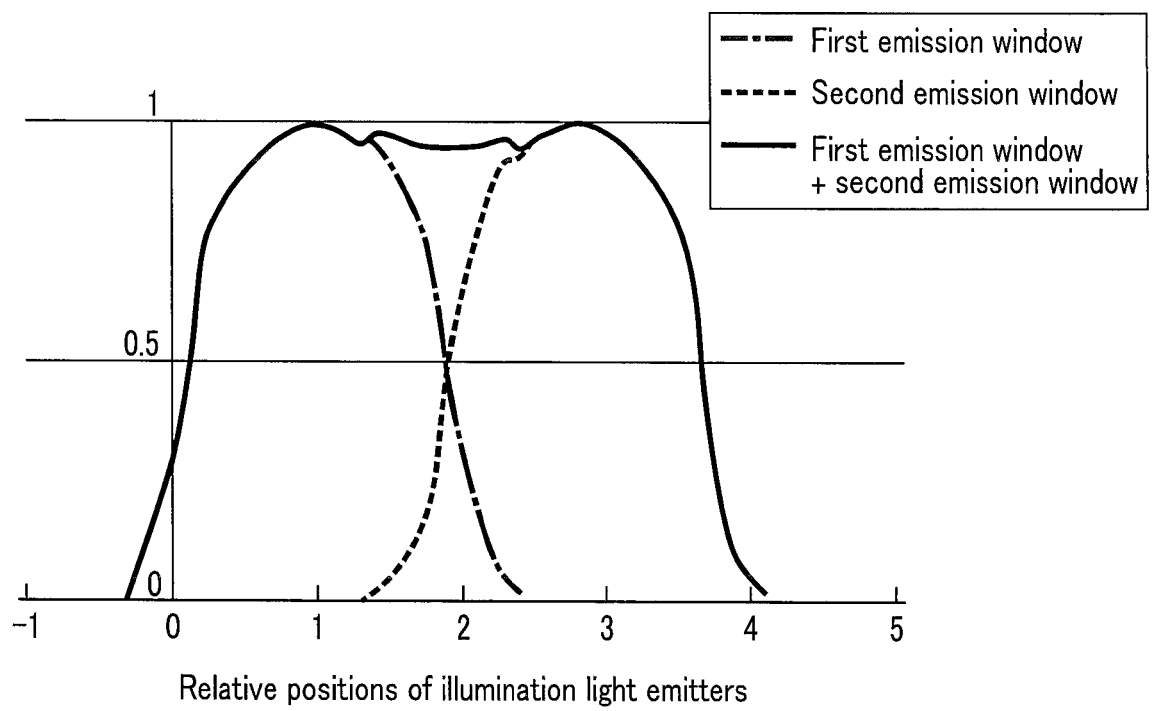
FIG. 11 is a graph showing an example of a light distribution of illumination lights emitted from two illumination light emitters in a non-bending state.
Figure 12:
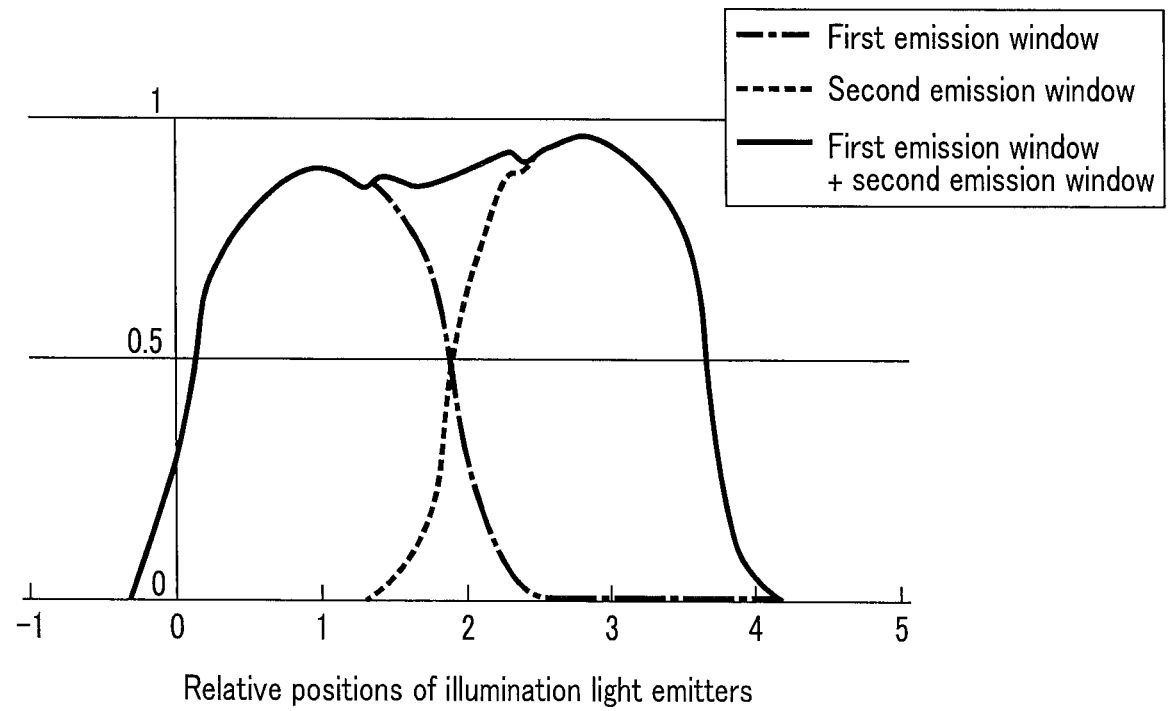
FIG. 12 is a graph showing an example of a light distribution of illumination lights emitted from the two illumination light emitters in a bending state.

FIG. 11 is a graph showing an example of light quantity distributions by the illumination lights emitted from the two illumination light emitters 115a and 115b when the insertion section 110 has a substantially straight shape. FIG. 12 is a graph showing an example of light quantity distributions by the illumination lights emitted from the two illumination light emitters 115a and 115b when the insertion section 110 is in a bending state shown in FIG. 10. Thus, the light quantity distributions (light distribution characteristics) of the illumination lights emitted from the two illumination light emitters 115a and 115b are substantially equal in a non-bending state, whereas the light quantity distributions of the two illumination light emitters 115a and 115b are different in a bending state, that is, the intensity distribution of the illumination light of the second light guide path 114b is relatively strong.

Therefore, in the present modification, the light distribution control circuit 54 transmits a control signal to the light distribution control member (in this case, the light distribution control member 119b), and the light distribution control member 119b controls the quantity of the illumination light, to decrease the quantity of the illumination light emitted from the second illumination light emitter 115b. The light distribution control circuit 54 adjusts the quantity of the illumination light to return the light quantity distributions (light distribution characteristics) of the illumination lights emitted from the two emission windows 117a and 117b to the distributions in a non-bending state shown in FIG. 11 from the distributions in a bending state shown in FIG. 12.

When the electronic diaphragms are used as the light distribution control members 119a and 119b, a reference table showing the relation between the opening diameters and decrease quantities of the diaphragms is stored in the storage 51, and an opening diameter is calculated from the difference of the light loss quantity between the first light guide path 114a and second light guide path 114b by the correction quantity calculation circuit 53. The correction quantity calculation circuit 53 transmits information on the calculated opening diameter to the light distribution control circuit 54, and the light distribution control circuit 54 transmits an opening diameter control signal to the light distribution control members 119a and 119b accordingly, so that the opening diameter is controlled.

When the variable-focus lenses are used as the light distribution control members 119a and 119b, the variable-focus lenses respectively provided in the illumination light emitters 115*a* and 115*b* are set to the same predetermined application voltage, and have the same focal distance in a non-bending state. In a bending state, after the drive electric current of the light source 30 is corrected to increase the illumination light quantity as in the first embodiment, the application voltage is reduced from the predetermined application voltage only in the variable-focus lens provided in the illumination light emitter (in this case, the illumination light emitter 115*b*) in which the illumination light quantity has increased from that in a non-bending state, so that the light collecting effect of the variable-focus lens is reduced, and the light quantity distribution (light distribution characteristic) is thus adjusted. A reference table showing the relation between the application voltage and the illumination light quantity distribution is stored in the storage 51, and an application voltage correction quantity is determined by the correction quantity calculation circuit 53 from the difference of the light loss quantity between the first light guide path 114*a* and second light guide path 114*b* and the information in the reference table.

Advantageous Effects

According to the present modification, even when the insertion section 110 is bent, the quantity and light quantity distributions (light distribution characteristics) of the illumination lights emitted from the two emission windows 117*a* and 117*b* can be corrected as in the case of no bending. Therefore, it is possible to provide the endoscope apparatus 1 in which the illumination light is more stably supplied and which enables more stable observation.

Second Embodiment

A second embodiment of the present invention is described with reference to FIG. 13 to FIG. 23. In the present embodiment, the light quantity, the light quantity ratio, the color temperature, and the color rendering index are controlled as the optical characteristics of the illumination lights. In the following explanation, components similar to those in the first embodiment are provided with the same reference marks and are not described, and configurations different from those in the first embodiment are only described.

FIG. 13 is a diagram schematically showing an endoscope apparatus 1*b* according to the second embodiment. The endoscope apparatus 1*b* has a light source unit 130 instead of the light source 30 in the first embodiment. The endoscope apparatus 1*b* also has an optical coupler 140 which optically couples the light source unit 130 to the light guide path 114. The endoscope apparatus 1*b* further has an illumination light controller 150 as a light quantity ratio controller.

(Light Source Unit)

The light source unit 130 comprises a first light source 131, a second light source 132, a third light source 133, and a fourth light source 134. These light sources 131, 132, 133, and 134 emit light of different wavelengths. The illumination light emitted from the illumination light emitter 115 is a mixed light which is a mixture of the lights different in wavelength emitted from the light sources 131, 132, 133, and 134. In the present embodiment, to emit white illumination light from the illumination light emitter 115, the light source unit 130 comprises a semiconductor laser light source (the first light source 131) which emits blue light, a semiconductor laser light source (the second light source 132) which emits green light, a semiconductor laser light source (the third light source 133) which emits yellow light, and a semiconductor laser light source (the fourth light source 134) which emits red light.

The semiconductor laser light source is not exclusively a direct-emission semiconductor laser which directly oscillates laser of a desired wavelength, but also includes an indirect-emission semiconductor laser light source which generates a second-order harmonic out of the light from the semiconductor laser. In the present embodiment, the third light source 133 which emits yellow light is the indirect-emission semiconductor laser light source in which a semiconductor laser that emits infrared light is combined with a non-linear optical element such as a PPLN. In the present embodiment, the light quantity ratios of the lights emitted from the respective light sources 131, 132, 133, and 134 are suitably combined, and the light quantity ratio is thereby set so that the color temperature which is one of the optical characteristics will be in the vicinity of 6000 K.

(Optical Coupler)

The light sources 131, 132, 133, and 134 are optically coupled to the optical coupler 140 by optical fibers 141, 142, 143, and 144 via an unshown lens, respectively. The entrance end of the light guide path 114 is also optically coupled to the optical coupler 140. Primary lights emitted from the light sources 131, 132, 133, and 134 are coupled to one light guide path 114 by the optical coupler 140.

The optical coupler 140 is an optical element having input ends and fewer output ends. In the present embodiment, the optical coupler 140 has four input ends and one output end. The optical coupler 140 can be an optical-fiber-type optical coupler which optically connects the end faces of optical fibers to the end face of one optical fiber, or an optical coupler which is a combination of dichroic mirrors or prisms. Otherwise, any configuration which can connect lights from more than one input end to fewer output ends may be used. In the present embodiment, the optical-fiber-type optical coupler is used.

(Optical Characteristic Converter)

An optical characteristic converter 116 which converts the optical characteristics of the primary light which propagates through the light guide path 114 is provided in the illumination light emitter 115. In the present embodiment, the optical characteristic converter 116 is a diffusion member, and increases the emission angle of the primary light which is emitted from the light source 30 and then propagates through the light guide path 114, and reduces coherence which is one of the optical characteristics of the primary light. In the present embodiment, the optical characteristic converter 116 does not convert the wavelength which is one of the optical characteristics, and emits, as illumination light, light having the same wavelength as that of the primary light, in contrast to the first embodiment.

In the present embodiment, as described above, primary lights emitted from the light sources (semiconductor lasers) which emit laser lights having different wavelengths are mixed in one light guide path 114, and applied to the observation target as illumination lights. Because the laser light has coherence, interference fringes may be produced in the irradiation surface of the observation target, and speckle noise may be produced in a reflection image. In this case, there is concern that an obtained observation image may be difficult to see. Thus, in the present embodiment, the diffusion member which diffuses the primary light is used as the optical characteristic converter 116 to reduce the coherence of each of the light sources 131, 132, 133, and 134. That is, the optical characteristic converter 116 converts (reduces) the coherence which is one of the optical characteristics of the primary light. The diffusion member also has a function which increases the spread angle of the illumination light which is another optical characteristic. The diffusion member does not convert the wavelengths of the lights emitted from the light sources 131, 132, 133, and 134 which are yet another optical characteristic.

(Light Quantity Ratio Controller)

The illumination light controller 150 has a storage 151, a curvature radius calculation circuit 152, and a correction quantity calculation circuit 153. The correction quantity calculation circuit 153 can instruct the light source controller 60 to change the light quantities of the respective four light sources 131, 132, 133, and 134 independently of each other. The correction quantity calculation circuit 153 can also instruct the light source controller 60 to increase or decrease the light quantities as a whole while maintaining the light quantities with respect to each other, that is, maintaining the mutual ratios of the light quantities.

In the present embodiment, the light source unit 130 comprises the four light sources 131, 132, 133, and 134, so that the light quantity control information indicating the relation between bending information for the insertion section 110 corresponding to the output of the curvature sensor 20 and the light emitted from the illumination light emitter 115 is prepared for each light source, and stored in the storage 151. FIG. 14 to FIG. 21 are reference tables showing examples of the light quantity control information for the respective light sources stored in the storage 151. As shown in FIG. 14 to FIG. 17, the storage 151 stores the relation between the curvature radius R of the insertion section 110 corresponding to the output of the curvature sensor 20, the quantity of the light emitted from the illumination light emitter 115 at the curvature radius R, and the change rate (decrease rate), that is, light guiding loss rate of the light quantity at the curvature radius R to that at a time of no bending, respectively. As shown in FIG. 18 to FIG. 21, the storage 151 also stores the relation between the curvature radius of the light guide path (optical fiber) 114 and the ratio of the light quantity at the curvature radius R of the insertion section 110 to that at the time of no bending, respectively. As shown in FIG. 14 to FIG. 17 and FIG. 18 to FIG. 21, the reference tables vary from wavelength to wavelength. Although not shown, the storage 151 further stores the relation between the curvature radius of the light guide path (optical fiber) 114 and the change rate (decrease rate) of the light quantity at this curvature radius to that at the time of no bending.

FIG. 22 is a table showing an example of information regarding each of the light sources 131, 132, 133, and 134 of the light source unit 130 stored in the storage 151. As shown in FIG. 22, the storage 151 stores the drive electric current Id of each of the light sources 131, 132, 133, and 134 at the time of no bending, and the threshold electric current Ith and element efficiency η of each of the light sources 131, 132, 133, and 134. The storage 151 also stores the relation between the drive electric current Ith of each of the light sources 131, 132, 133, and 134 and the light output P, and the relation between the light guiding loss rate α and the drive electric current correction value ΔId.

(Operation)

The control operation of the illumination light in the endoscope apparatus 1b according to the second embodiment is described.

When primary lights are emitted from the respective light sources 131, 132, 133, and 134 of the light source unit 130, these primary lights enter the optical coupler 140 through the optical fibers 141, 142, 143, and 144, respectively. The primary lights that have entered are mixed into one by the optical coupler 140, and then enter one light guide path 114. The primary lights that have entered are propagated to the optical characteristic converter (diffusion member) 116 provided in the illumination light emitter 115 through the light guide path 114. As described above, the diffusion member reduces the coherence of the primary lights, and converts their optical characteristics to increase the spread angle. The wavelengths of the primary lights are not converted. As a result, a mixed light which is a mixture of four single-color lights different in wavelength is emitted from the emission window 117 as illumination light.

When the insertion section 110 is bent, the light guide path 114 attached to the insertion section 110 also changes its bending shape accordingly. In this instance, different light guiding losses are caused to the four primary lights which propagate through the light guide path 114, in accordance with the wavelengths of the respective primary lights. If the curvature radius R decreases, the light loss quantities of all the primary lights increase, but the light loss quantities vary from each other depending on the wavelengths. Therefore, the illumination light emitted from the emission window 117 not only becomes darker but also changes color due to the bending of the insertion section 110. In other words, the light quantity decreases due to the bending of the insertion section 110, and in addition, the light quantity ratio changes, so that the color temperature or color rendering index which is one of the optical characteristics of the illumination light changes.

The curvature sensor 20 outputs the bending shape information for the insertion section 110 to the curvature radius calculation circuit 152 as a detection signal. In a process similar to that in the first embodiment, the curvature radius calculation circuit 152 calculates the curvature radius R of the part of the insertion section 110 having the greatest curvature radius R, and outputs information on this the curvature radius R to the correction quantity calculation circuit 153. On the basis of this curvature radius R, the correction quantity calculation circuit 153 calculates light loss quantities at the curvature radius R by referring to the light quantity control information for the respective light sources stored in the storage 151 (e.g. the reference tables shown in FIG. 14 to FIG. 17 and FIG. 18 to FIG. 21). That is, the correction quantity calculation circuit 153 respectively extracts the light loss quantities wavelength by wavelength, that is, for the respective light sources 131, 132, 133, and 134 by referring to FIG. 14 to FIG. 17 and FIG. 18 to FIG. 21, and calculates a drive electric current quantity correction quantity for each of the light sources accordingly. The correction quantity calculation circuit 153 then outputs the drive electric current correction signal to the light source controller 60. On the basis of the drive electric current correction quantity, the light source controller 60 controls the quantity of the primary light emitted from each of the light sources 131, 132, 133, and 134 of the light source unit 130 so that the light quantity, color temperature, and color rendering index of the illumination light which are optical information for the illumination light emitted from the illumination light emitter 115 will be substantially the same as the light quantity, the color temperature, and the color rendering index of the illumination light emitted from the illumination light emitter 115 when the insertion section 110 is not bent. That is, the light source controller 60 independently adjusts the light quantity of each light source.

As a specific example of white illumination light, described is the light source unit 130 (white illumination light device) in which the first light source 131 is a blue light emitting semiconductor laser having a wavelength of 445 nm and an output of 250 mW, the second light source 132 is a green light emitting semiconductor laser having a wavelength of 525 nm and an output of 225 mW, the third light source 133 is a red light emitting semiconductor laser having a wavelength of 638 nm and an output of 500 mW, and the fourth light source 134 is a yellow light emitting semiconductor laser having a wavelength of 560 nm and an output of 125 mW. The light guide path 114 is a multimode optical fiber having a core diameter of 50 μm, and the optical characteristic converter 116 is a diffusion member in which an alumina filler is added to a glass-based transparent material.

The blue light, the green light, the red light, and the yellow light (a total light quantity of 1100 mW, and a light quantity ratio of 1:0.9:2:0.5) which are the primary lights emitted from the respective light sources 131, 132, 133, and 134 propagate through the light guide path 114 and the optical coupler 140, and enter the optical characteristic converter 116 from the optical fibers 141, 142, 143, and 144 via the unshown lens, respectively. The primary lights are converted into secondary lights having reduced coherence by the optical characteristic converter 116, and illumination light having mixed colors (color temperature~6000 K) is emitted from the illumination light emitter 115. The explanation is continued below so that the conversion efficiency with which the light emitted from the light source unit 130 is emitted as the illumination light from the illumination light emitter 115 as described above is estimated at 64%.

For example, when the curvature radius R of the insertion section 110 is estimated at 20 mm by the curvature radius calculation circuit 152, the correction quantity calculation circuit 153 reads, on the basis of this estimation, the change rates (light guiding loss rates) of the respective light sources 131, 132, 133, and 134 to those at times of no bending from the light quantity control information for each light source shown in FIG. 14 to FIG. 17, so that the blue light is 4.5%, the green light is 4.4%, the red light is 3.0%, and the yellow light is 6.6%, respectively, and the total light quantity decreases by about 4.1%. The light quantity ratio of the light sources 131, 132, 133, and 134 is 0.98:0.89:2:0.48. The light quantity ratio of the respective colors as the white illumination lights is small in fluctuation, but the decrease of the yellow light is 4%, and the color temperature decreases to about 5800 K. However, because the fluorescent material is not combined, the change in the shape of the whole spectrum of the white light is small, so that color rendering is considered negligible. Nevertheless, the green light and the yellow light that constitute the white light are high in visibility, so that there is a possibility that the color change of the image may affect the observation image (image diagnosis) in a bending state.

Therefore, the correction quantity calculation circuit 153 calculates the drive electric current correction quantity which increases the light output, for the initially set light output independently of each light source which emits primary light. The correction quantity calculation circuit 153 sends the drive electric current correction signal to the light source controller 60, and controls so that the output of the semiconductor laser of each of the light sources 131, 132, 133, and 134 will be increased to compensate for the light loss quantity, and the total quantity and light quantity ratio of the illumination lights will be kept at predetermined values.

For example, the correction quantity calculation circuit 153 calculates the drive electric current correction quantity so that the light quantity of the third light source 133 having a high light quantity ratio will be substantially equal to the light quantity at the time of no bending, and the correction quantity calculation circuit 153 sends the drive electric current correction signal to the light source controller 60. The light source controller 60 then returns the quantity of the red light in the illumination lights to the light quantity at the time of no bending. The light source controller 60 then adjusts the light quantity ratio of the respective light sources 131, 132, 133, and 134 so that the color temperature will be 6000 K±100 K. That is, the light source controller 60 controls the fluctuation of the light quantity ratio of the central wavelengths emitted from the respective light sources 131, 132, 133, and 134 so that the color temperature will be within the range of color coordinates (x, y) included in a range indicated by a frame F in FIG. 23.

Specifically, the storage 151 stores the reference table showing the relation between the light quantity ratio and color temperatures of the respective light sources 131, 132, 133, and 134, for example, as shown in FIG. 24. The correction quantity calculation circuit 153 reads this relation, and then independently sets correction electric current quantities for the light quantity ratio of the respective light sources 131, 132, 133, and 134 so that the change quantity of the color temperature will be within a color temperature change allowable range of 6000±100 K. For example, it is possible to obtain a satisfactory observation environment by controlling so that the change of the color temperature will be in the color temperature change allowable range or less. It is also possible to obtain a satisfactory observation environment if a color temperature change quantity is ±50 K or less. Moreover, it is possible to obtain a substantially satisfactory observation environment if a color temperature change quantity is ±100 K or less.

Advantageous Effects

According to the present embodiment, when light sources different in wavelengths are used, it is possible to obtain the endoscope apparatus 1*b* which controls the color temperature change allowable range and the color rendering index change allowable range within predetermined allowable ranges by compensating for the light loss quantity for each wavelength of the primary light caused by bending independently for each light source, and supplies stable illumination lights, even if the insertion section 110 is bent.

Third Embodiment

A third embodiment of the present invention is described with reference to FIG. 25 to FIG. 29. In the following explanation, components similar to those in the second embodiment are provided with the same reference marks and are not described, and configurations different from those in the second embodiment are only described.

FIG. 25 is a diagram schematically showing an endoscope apparatus 1*c* according to the third embodiment. The endoscope apparatus 1*c* has two light source units 130 and 160, two optical couplers 140 and 170, two light guide paths 114*c* and 114*d*, and two illumination light emitters 115*c* and 115*d*. Optical characteristic converters 116*c* and 116*d* respectively provided in the illumination light emitters 115*c* and 115*d* are diffusion members, as in the second embodiment. In the third embodiment, the light quantity, the light quantity ratio, the color temperature, the color rendering index, and the light quantity distributions, that is, light distribution characteristics of the illumination lights independently emitted from the two light guide paths 114c and 114d are controlled as the optical characteristics of the illumination lights.

(Light Source Unit)

Similarly to the light source unit 130 in the second embodiment, the first light source unit 130 comprises the light sources 131, 132, 133, and 134, and these light sources are semiconductor laser light sources which emit lights having wavelengths different from one another. The second light source unit 160 comprises a fifth light source 161, a sixth light source 162, a seventh light source 163, and an eighth light source 164. The light sources 161, 162, 163, and 164 are semiconductor laser light sources which emit lights having wavelengths substantially equal to those of the light sources 131, 132, 133, and 134, respectively. The wavelengths, the light quantity ratio to produce white light, and others are also similar to those in the second embodiment. The first light source unit 130 is optically connected the optical coupler 140, the light guide path 114c, and the illumination light emitter 115c, and the second light source unit 160 is optically connected the optical coupler 170, the light guide path 114d, and the illumination light emitter 115d.

The light guide path 114c, the light guide path 114d, and the curvature sensor 20 are provided in the insertion section 110. The light guide path 114c, the light guide path 114d, and the curvature sensor 20 are different from one another in the curvature radius resulting from the bending of the insertion section 110, as in the modification of the first embodiment.

In the present embodiment as well, the light quantity control information indicating the relation between the bending information for the insertion section 110 corresponding to the output of the curvature sensor 20 and the illumination lights emitted from the illumination light emitters 115c and 115d is prepared for each light source, and stored in the storage 151. FIG. 26 and FIG. 27 are reference tables showing examples of the light quantity control information for the light source units 130 and 160 stored in the storage 151, respectively. The storage 151 stores the relation between the curvature radius R of the insertion section 110 corresponding to the output of the curvature sensor 20, the quantities of the lights emitted from the illumination light emitters 115c and 115d at the curvature radius R, the quantity of the illumination light (total light quantity), and the change rate (decrease rate), that is, light guiding loss rate of the light quantity at the curvature radius R to that at the time of no bending, respectively (the light guiding loss rate is not shown in FIG. 26 and FIG. 27). As shown in FIG. 28, the storage 151 also stores the relation between the curvature radius of the light guide path (optical fiber) 114, and the ratios of the light quantities of the respective light sources 131, 132, 133, 134, 161, 162, 163, and 164 at the curvature radius R of the insertion section 110 to those at times of no bending, respectively. Although not shown, the storage 151 further stores the relation between the curvature radius of the light guide path (optical fiber) 114, and the change rate (decrease rate) of the light quantity at this curvature radius to that at the time of no bending.

FIG. 29 is a table showing an example of information regarding the light source units 130 and 160 stored in the storage 151. As shown in FIG. 29, the storage 151 stores the drive electric current Id of each of the light sources at the time of no bending, and the threshold electric current Ith and element efficiency η of each of the light sources. The storage 151 also stores the relation between the drive electric current Ith of each of the light sources and the light output P, and the relation between the light guiding loss rate α and the drive electric current correction value ΔId.

(Operation)

The basic operation is similar to that in the second embodiment. As described above, the present embodiment is different from the second embodiment in that the two light guide paths 114c and 114d are provided in the insertion section 110, and are slightly different from each other including their curvature radii which are detected by the curvature sensor 20. That is, when the insertion section 110 is bent, the illumination light guided by the light guide path disposed on the side where the curvature radius is smaller is higher in light loss quantity than the illumination light guided by the light guide path disposed on the side where the curvature radius is larger. That is, the same as that in the modification of the first embodiment holds true (see FIG. 10 to FIG. 12).

Particularly in the modification of the first embodiment, the optical characteristic converters 116a and 116b are fluorescent materials, so that a light quantity difference of several percent of white light is difficult to recognize and therefore does not easily become a problem even if the curvature radii of the light guide paths 114a and 114b are different. However, when the optical characteristic converters 116c and 116d are diffusion members and the laser light of each color is applied as it is as in the present embodiment, a difference of color tones is made and can become a problem if the curvature radii of the light guide paths 114a and 114b are different.

Thus, in the present embodiment as well as in the modification of the first embodiment, the curvature radius calculation circuit 152 receives a detection signal from the curvature sensor 20, and then calculates the curvature radius R1 of the curvature sensor 20. The curvature radius calculation circuit 152 further reads the information on the positional relation between the first light guide path 114c, the second light guide path 114d, and the curvature sensor 20 stored in the storage 51. The curvature radius calculation circuit 152 then calculates the curvature radius R2 of the first light guide path 114c and the curvature radius R3 of the second light guide path 114d on the basis of the curvature radius R1 of the curvature sensor 20 and the read positional relation information, and outputs information on the curvature radii R2 and R3 to the correction quantity calculation circuit 153.

As in the modification of the first embodiment, the correction quantity calculation circuit 153 reads, from the storage 151, the light loss quantities of the respective light sources 131, 132, 133, 134, 161, 162, 163, and 164, that is, information on the relation between the curvature radius and the light quantity ratio for each of the curvature radii R2 and R3, and drive electric current values for the respective light sources, by referring to the light quantity control information indicating the relation between the bending state information for each emission window stored in the storage 151, and the quantities of the illumination lights emitted from the illumination light emitters 115c and 115d for the respective emission windows. The correction quantity calculation circuit 153 calculates the drive electric current correction quantity for each light source from the above information, and outputs the drive electric current correction signal to the light source controller 60. The light source controller 60 controls the light sources 131, 132, 133, 134, 161, 162, 163, and 164 on the basis of the drive electric current correction quantity.

Advantageous Effects

According to the present embodiment, even when the insertion section 110 is bent, the light quantity, color temperature, color rendering index, and others of the illumination lights emitted from the two emission windows 117c and 117d can be corrected to be substantially equal to those when the insertion section is not bent. Therefore, it is possible to provide the endoscope apparatus 1c in which the illumination light is more stably supplied and which enables more stable observation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
   a light source;
   a bendable insertion section to be inserted into an observation target;
   a light guide path which is provided in the insertion section and which guides light emitted from the light source to a distal end of the insertion section where at least some of the light guided by the light guide path is emitted to the observation target as illumination light;
   a curvature sensor which detects a bending shape of at least a part of the insertion section; and
   an illumination light controller is configured to:
      receive a signal from the curvature sensor indicating a detected bending shape of at least the part of the insertion section; and
      when the signal indicates at least the part of the insertion section is bent at a radius of curvature, control the light source to adjust a quantity of illumination light emitted from the distal end based on the signal;
      wherein the adjustment is based on light quantity control information including at least a quantity of illumination light emitted from the distal end at the radius of curvature, and a change rate of an illumination light quantity at the radius of curvature as compared to when at least the part of the insertion section is in a straight shape.

2. The endoscope apparatus according to claim 1, wherein the adjustment is further based on at least one of a light quantity, a light quantity ratio, a color temperature, a color rendering index, and a light distribution characteristic.

3. The endoscope apparatus according to claim 1, wherein the illumination light controller adjusts the quantity of the illumination light such that the quantity of the illumination light at the detected radius of curvature becomes a light quantity substantially equal to a light quantity when at least the part of the insertion section is in the straight state.

4. The endoscope apparatus according to claim 1, wherein the illumination light controller comprises a light quantity change allowable range to control the quantity of the illumination light to a predetermined change quantity or less when the bending shape of at least the portion of the insertion section changes.

5. The endoscope apparatus according to claim 1, further comprising an operation quantity sensor which detects an input operation quantity for operating the bending shape of at least the part of the insertion section.

6. The endoscope apparatus according to claim 1, wherein the curvature sensor is a fiber sensor or a magnetic sensor which detects the bending state of at least the part of the insertion section.

7. The endoscope apparatus according to claim 1, wherein the bending shape to be detected by the curvature sensor is a bending quantity of at least the part of the insertion section.

8. The endoscope apparatus according to claim 1, further comprising a illumination light emitter provided at the distal end of the insertion section, the illumination light emitter being configured to emit at least some of the light guided by the light guide path to the observation target as illumination light.

9. The endoscope apparatus according to claim 8, wherein the illumination light controller comprises a storage which stores the light quantity control information.

10. The endoscope apparatus according to claim 9, wherein the illumination light emitter comprises a plurality of illumination light emitters, and
   the controller is configured to adjust the quantity of the illumination light for each of the plurality of illumination light emitters.

11. The endoscope apparatus according to claim 10, wherein the illumination light controller comprises a light quantity change allowable range to control so that the quantity of the illumination light is within at least one of a color temperature change allowable range and a color rendering index change allowable range when the bending shape of at least the portion of the insertion section changes.

12. The endoscope apparatus according to claim 11, wherein the light quantity control information comprises information indicating a relation between a curvature radius of the light guide path and the ratio of the quantity of the illumination light emitted from the light source at the curvature radius of at least the part of the insertion section to that at the straight shape
   information indicating the relation between the curvature radius of the light guide path and the ratio of the quantity of the emitted light at the curvature radius of the light guide path to that at the straight shape.

13. A controller for controlling a light source providing light to a bendable insertion section that emits at least some of the light to an observation target as illumination light, the controller being configured to:
   receive a signal from a curvature sensor indicating a detected bending shape of at least a part of the insertion section; and
   when the signal indicates at least the part of the insertion section is bent at a radius of curvature, control the light source to adjust a quantity of illumination light emitted from the insertion section based on the signal;
   wherein the adjustment is based on light quantity control information including at least a quantity of illumination light emitted from the insertion section at the radius of curvature, and a change rate of an illumination light quantity at the radius of curvature as compared to when at least the part of the insertion section is in a straight shape.

14. The endoscope apparatus according to claim 13, wherein the light source comprising a plurality of light sources each emitting light of a different in wavelength band,
   the illumination light is a mixed light which is a mixture of the lights different in wavelength band that are emitted from the plurality of light sources,
   the change rate of the illumination light quantity comprises light quantity information for each of the lights different in wavelength band that are emitted from the illumination light emitter, and
   the illumination light controller independently controls a light quantity ratio of the lights different in wavelength band for each of the plurality of light sources on the basis of the change rate of the illumination light quantity so that the color of the illumination light becomes substantially equal to the color of the illumination light in the straight state.

15. The endoscope apparatus according to claim 14, wherein the light source comprising a plurality of light sources, each emitting light of a different in wavelength band,
- the illumination light emitter comprises a plurality of illumination light emitters,
- the illumination light is a mixed light which is a mixture of the lights different in wavelength band that are emitted from the plurality of light sources,
- the change rate of the illumination light quantity for each of the plurality of illumination light emitters comprises change rate of the illumination light quantity for each of the lights different in wavelength band that are emitted from the plurality of illumination light emitters, and
- the illumination light controller independently adjusts the quantity of the illumination light of the lights different in wavelength band for each of the plurality of light sources on the basis of the change rate of the illumination light quantity for each of the plurality of illumination light emitters so that the color of the illumination light of each of the plurality of illumination light emitters becomes substantially equal to the color of the illumination light in the straight state.

* * * * *